US012622928B2

(12) United States Patent
Kim et al.

(10) Patent No.: US 12,622,928 B2
(45) Date of Patent: May 12, 2026

(54) NANOVESICLES FROM ADULT STEM CELLS AND ITS USE FOR TARGETED THERAPY

(71) Applicants: SEOUL NATIONAL UNIVERSITY R&DB FOUNDATION, Seoul (KR); SUNGKWANG MEDICAL FOUNDATION, Seoul (KR)

(72) Inventors: Byung-Soo Kim, Seoul (KR); Han Young Kim, Seoul (KR); In Bo Han, Seoul (KR); Hemant Kumar, Seoul (KR)

(73) Assignees: Seoul National University R&DB Foundation, Seoul (KR); Sungkwang Medical Foundation, Seoul (KR)

( * ) Notice: Subject to any disclaimer, the term of this patent is extended or adjusted under 35 U.S.C. 154(b) by 1417 days.

(21) Appl. No.: 16/966,383

(22) PCT Filed: Jan. 29, 2019

(86) PCT No.: PCT/KR2019/001214
§ 371 (c)(1),
(2) Date: Jan. 27, 2021

(87) PCT Pub. No.: WO2019/151744
PCT Pub. Date: Aug. 8, 2019

(65) Prior Publication Data
US 2022/0249570 A1     Aug. 11, 2022

(30) Foreign Application Priority Data

Jan. 31, 2018    (KR) ........................ 10-2018-0011928
Jan. 28, 2019    (KR) ........................ 10-2019-0010380

(51) Int. Cl.
| | |
|---|---|
| *A61K 35/28* | (2015.01) |
| *A61K 9/00* | (2006.01) |
| *A61K 9/127* | (2006.01) |
| *A61K 41/00* | (2020.01) |
| *A61K 47/02* | (2006.01) |
| *A61P 25/28* | (2006.01) |
| *C12N 5/0775* | (2010.01) |

(52) U.S. Cl.
CPC ........... *A61K 35/28* (2013.01); *A61K 9/0019* (2013.01); *A61K 9/127* (2013.01); *A61K 41/00* (2013.01); *A61K 47/02* (2013.01); *A61P 25/28* (2018.01); *C12N 5/0662* (2013.01); *C12N 2500/24* (2013.01)

(58) Field of Classification Search
None
See application file for complete search history.

(56) References Cited

U.S. PATENT DOCUMENTS

| | | | |
|---|---|---|---|
| 2013/0071326 | A1 | 3/2013 | Martinez et al. |
| 2015/0045298 | A1 | 2/2015 | Bang et al. |

FOREIGN PATENT DOCUMENTS

| | | |
|---|---|---|
| KR | 1020130019356 A | 6/2014 |
| KR | 1020170010956 A | 2/2017 |
| KR | 1020180003322 A | 1/2018 |
| WO | 2018004143 A1 | 1/2018 |

OTHER PUBLICATIONS

Jang (ACS Nano (2013), vol. 7, No. 9, pp. 7698-7710).*
"Artificial" definition (https://www.merriam-webster.com/dictionary/artificial)—accessed Oct. 2024.*
Weinstein et al., "Superparamagnetic iron oxide nanoparticles: diagnostic magnetic resonance imaging and potential therapeutic applications in neurooncology and central nervous system inflammatory pathologies, a review", Journal of Cerebral Blood Flow & Metabolism (2010) 30, 15-35.
Hu et al., "Magnetic Resonance Imaging of Melanoma Exosomes in Lymph Nodes", Magnetic Resonance in Medicine 74:266-271 (2015).
Pal et al., "Iron oxide nanoparticles and magnetic field exposure promote functional recovery by attenuating free radical-induced damage in rats with spinal cord transection", International Journal of Nanomedicine 2013:8 2259-2272.
International Search Report for corresponding PCT Application No. PCT/KR2019/001214 mailed May 8, 2019.
First Office Action for corresponding Korean Application No. 10-2019-0010380 mailed May 4, 2020.
Altanerova et al., "Human mesenchymal stem cell-derived iron oxide exosomes allow targeted ablation of tumor cells via magnetic hyperthermia", International Journal of Nanomedicine 2017:12, 7923-7936.

(Continued)

*Primary Examiner* — Susan Hoffman
(74) *Attorney, Agent, or Firm* — Wood, Phillips, Katz, Clark & Mortimer

(57) ABSTRACT

Disclosed herein is a nanovesicles from adult stem cells containing iron nanoparticles and its use. The nanovesicle according to the present disclosure provides effects of maximizing the efficacy of treating mesenchymal stem cells by pretreating cells with iron nanoparticles; reconstituting the cells in a nano-sized form to facilitate intravenous injection; and increasing the efficiency of targeting disease areas through magnet induction. In particular, the present disclosure can replace mesenchymal stem cells as a cell therapeutic agent, and it can be applied to various diseases as a novel biopharmaceutical drug because it can increase the function and efficiency of an exosome-based therapeutic agent.

17 Claims, 13 Drawing Sheets

(56)             References Cited

OTHER PUBLICATIONS

Busato et al., "Magnetic resonance imaging of ultrasmall superparamagnetic iron oxide-labeled exosomes from stem cells: a new method to obtain labeled exosomes", International Journal of Nanomedicine 2016:11 2481-2490.

Kim et al., "Therapeutic Efficacy-Potentiated and Diseased Organ-Targeting Nanovesicles Derived from Mesenchymal Stem Cells for Spinal Cord Injury Treatment", Nano Lett. 2018, 18, 4965-4975.

* cited by examiner

【FIG 1】
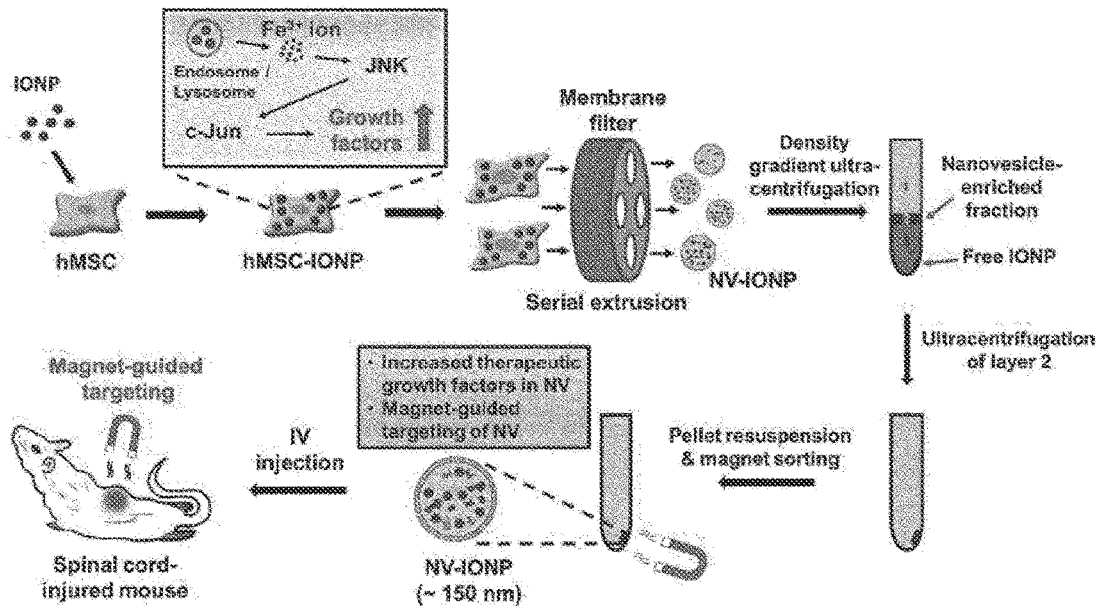
【FIG 2】
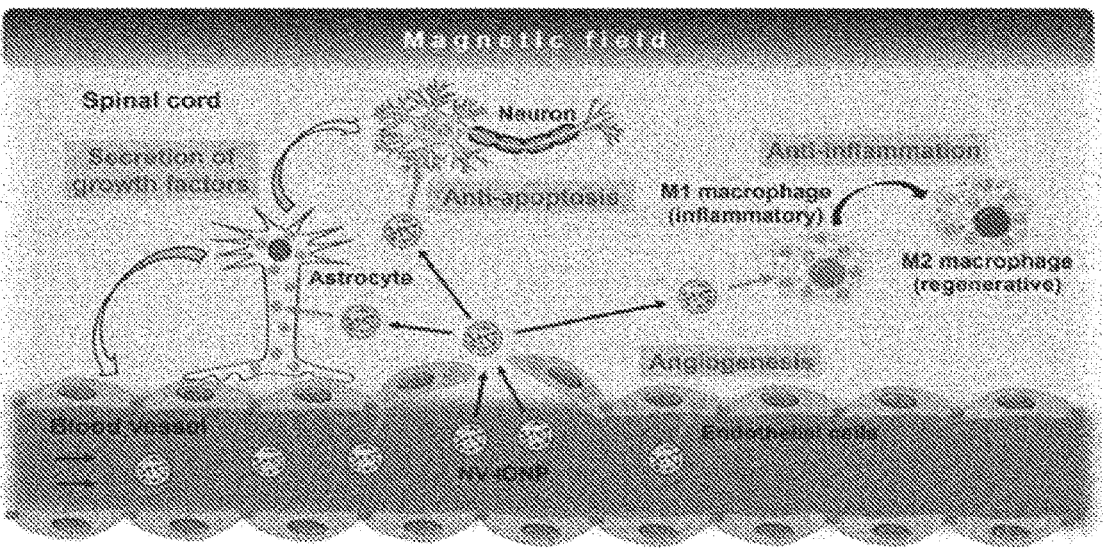
【FIG 3】
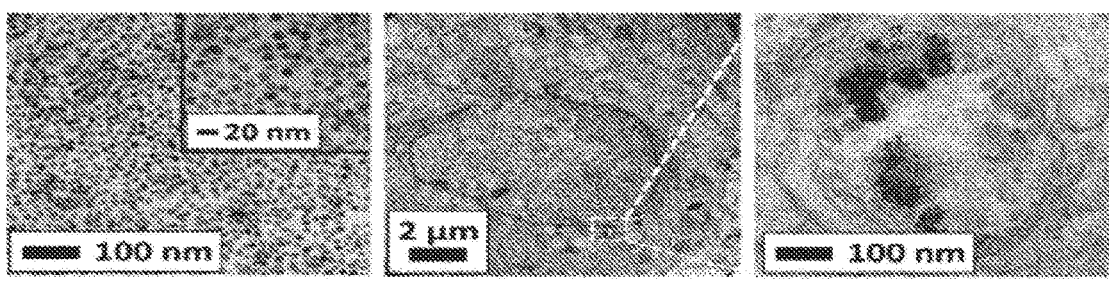

【FIG 4】
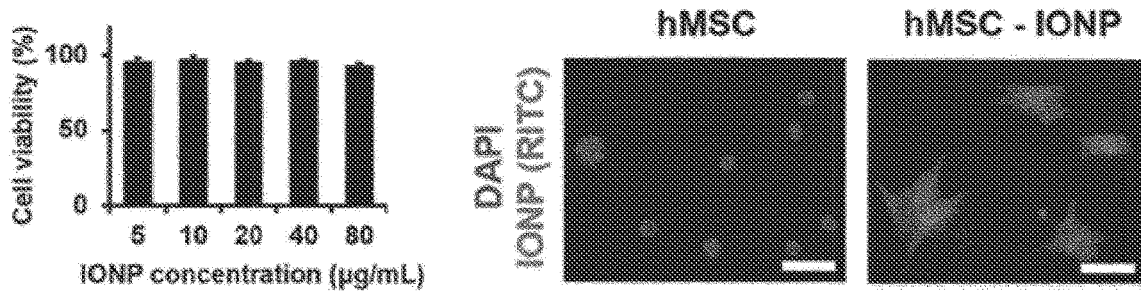
【FIG 5】
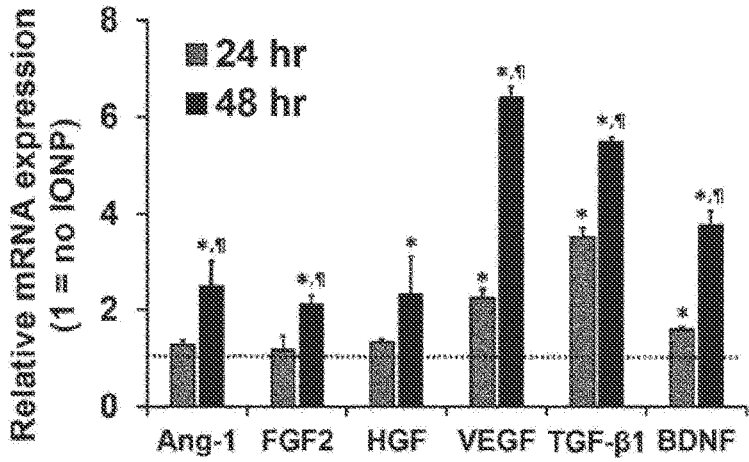
【FIG 6】
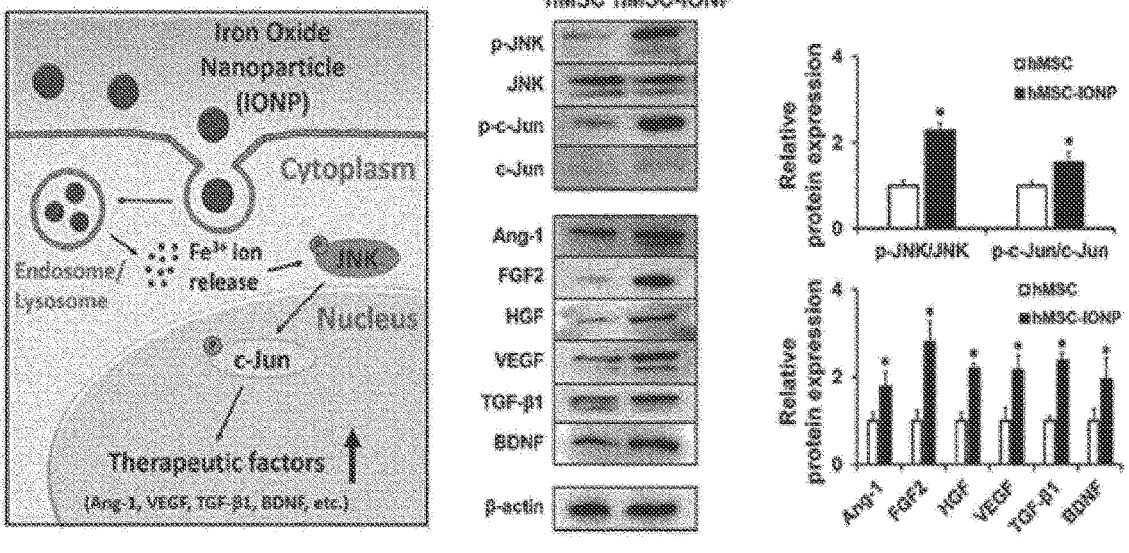

【FIG 7】
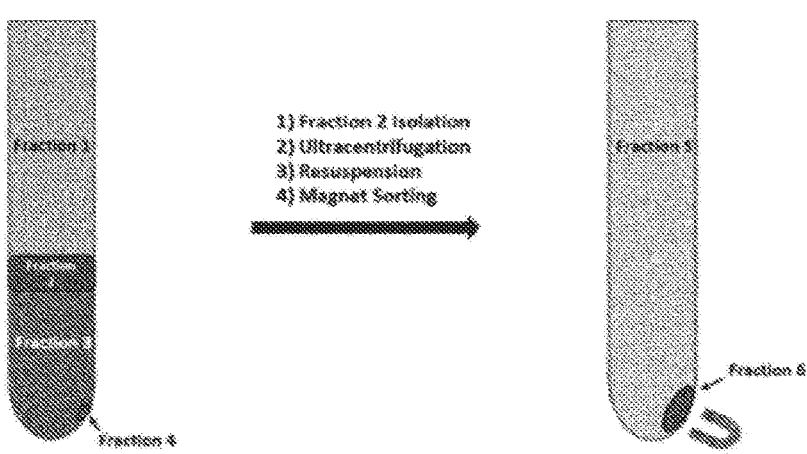
【FIG 8】
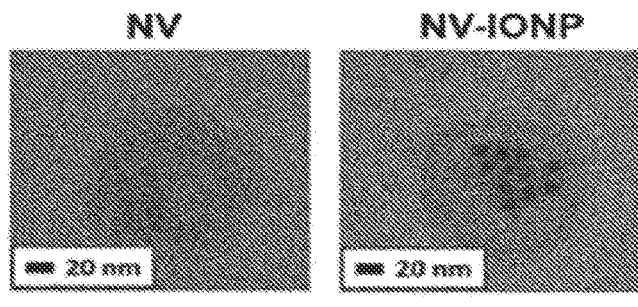
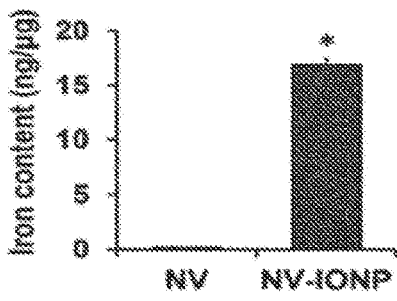
【FIG 9】
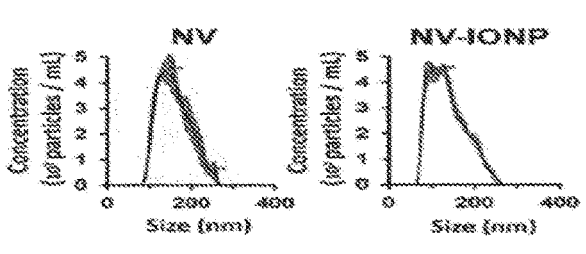
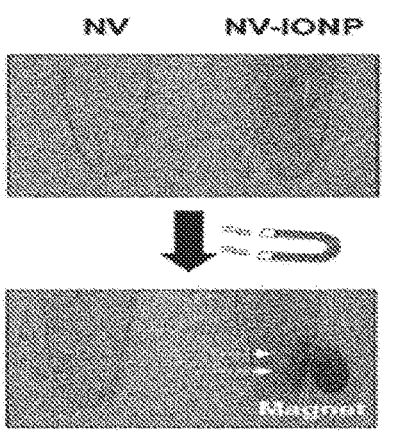

【FIG 10】
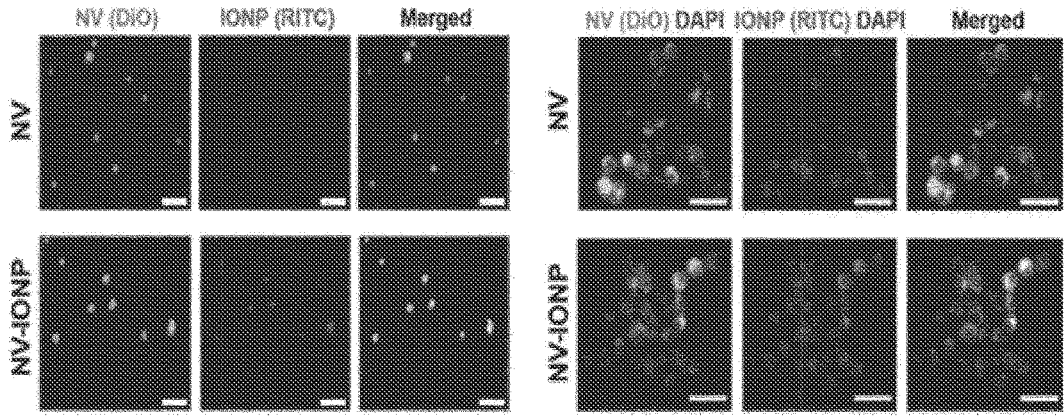
【FIG 11】
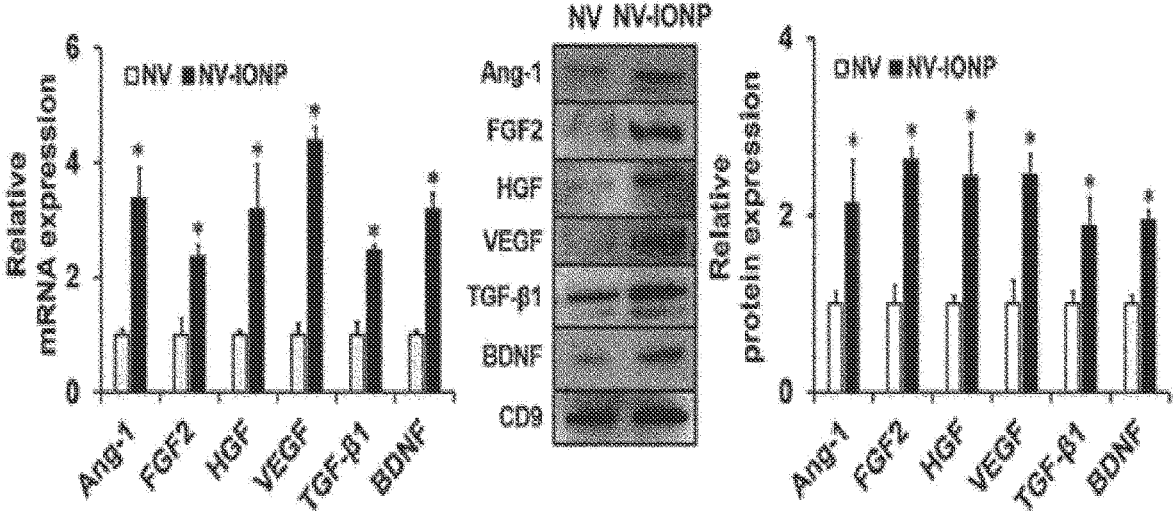

【FIG 12】
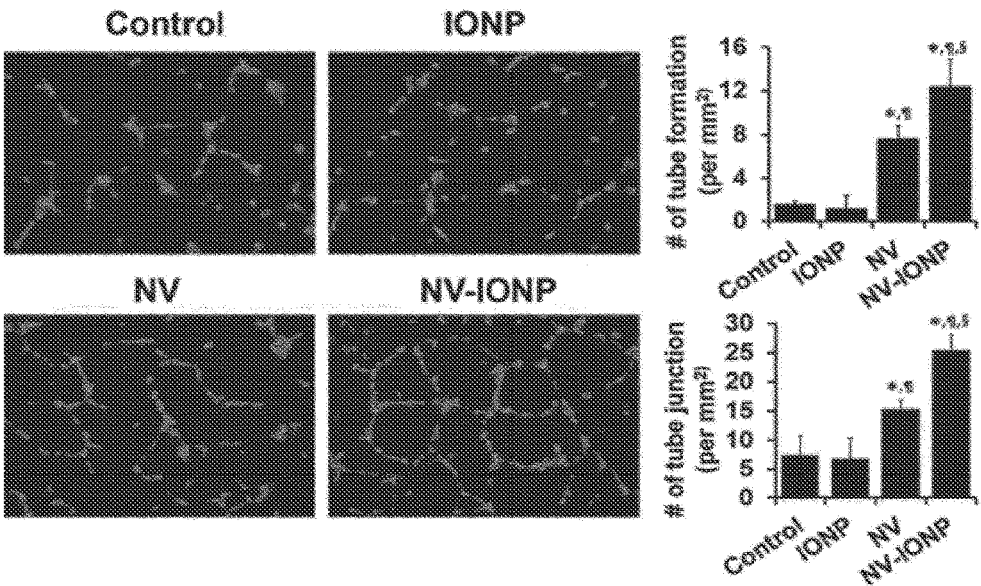
【FIG 13】
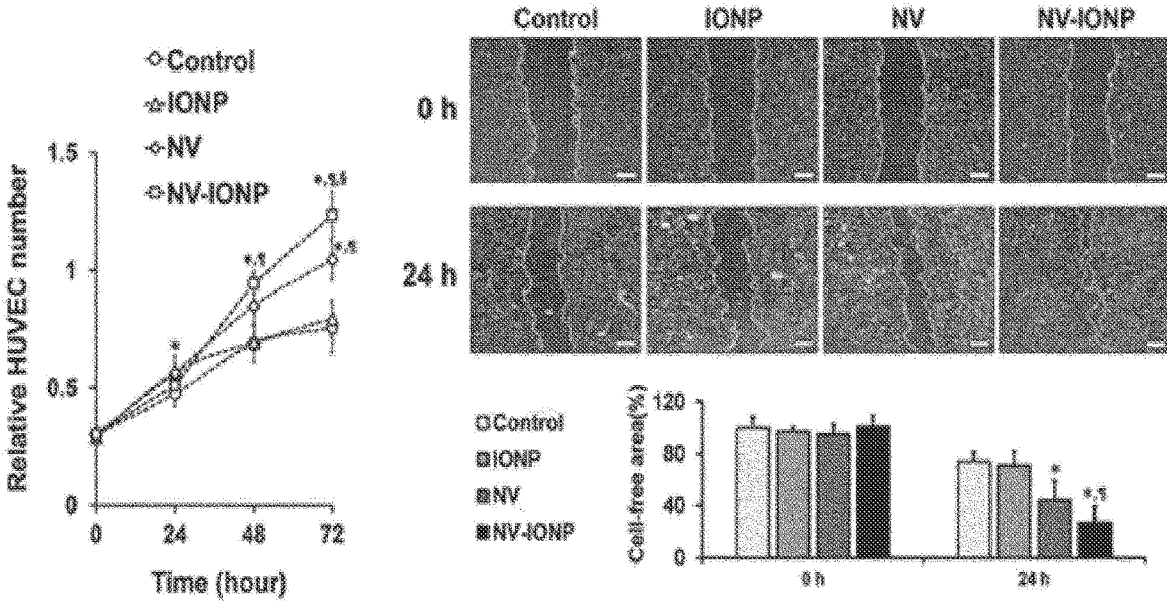

【FIG 14】
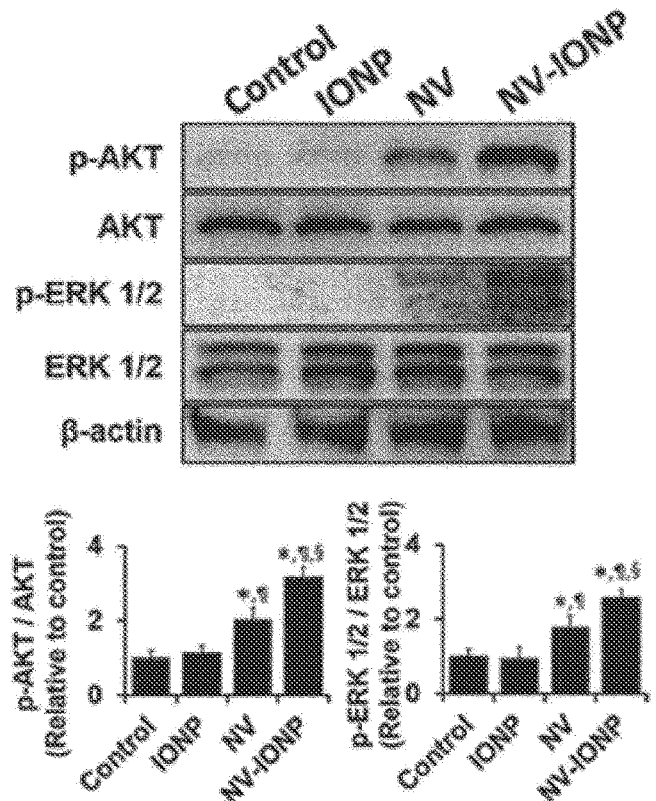
【FIG 15】
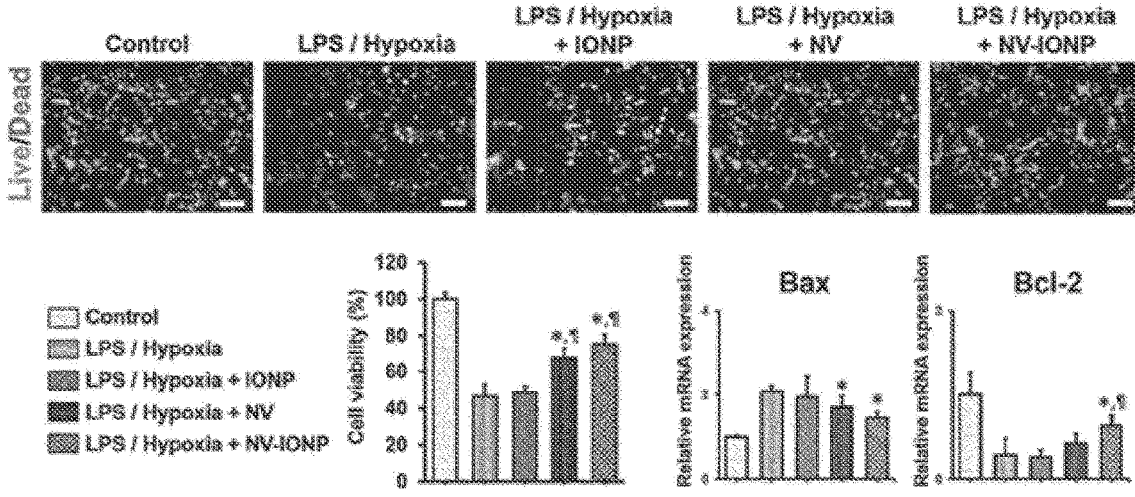

【FIG 16】
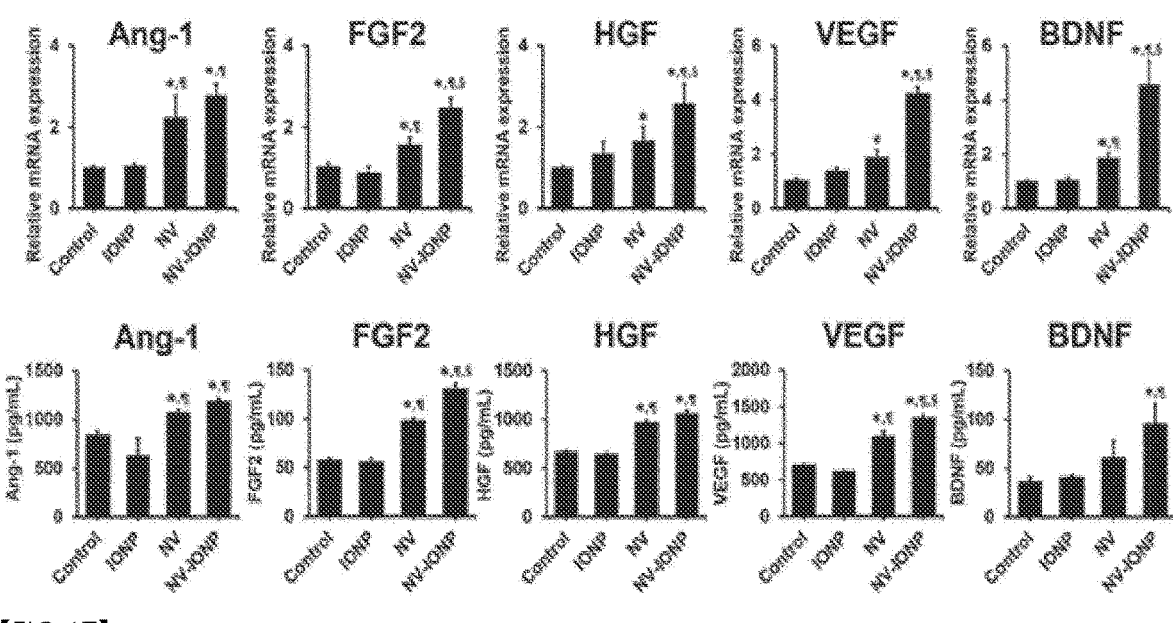
【FIG 17】
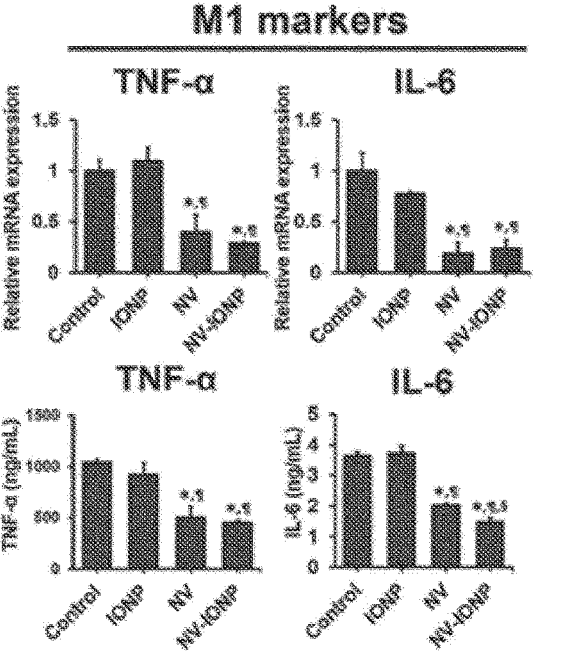
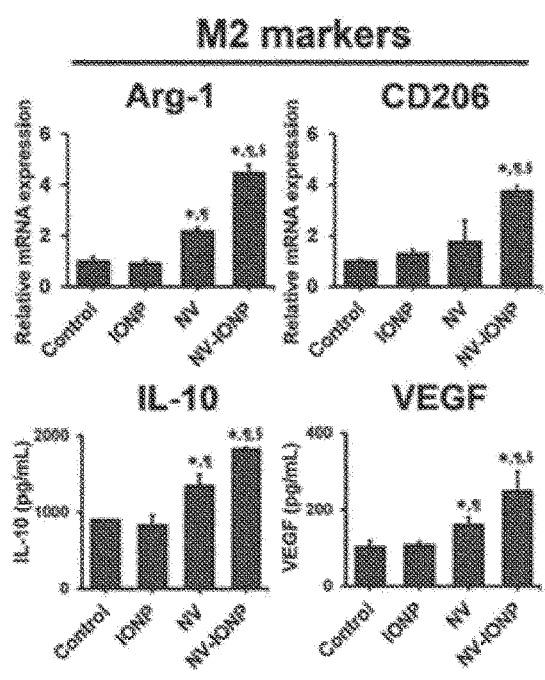

【FIG 18】
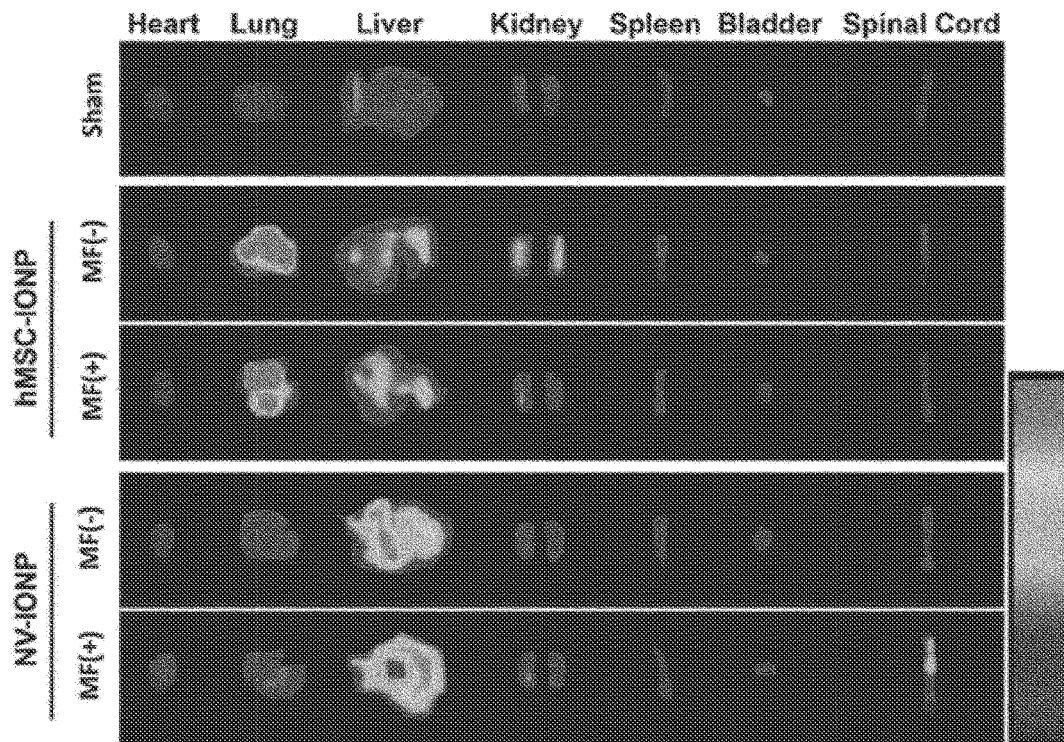
【FIG 19】
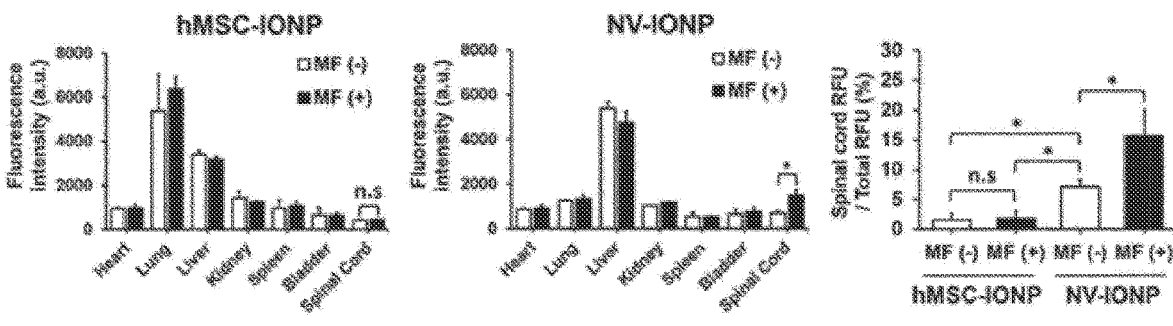
【FIG 20】
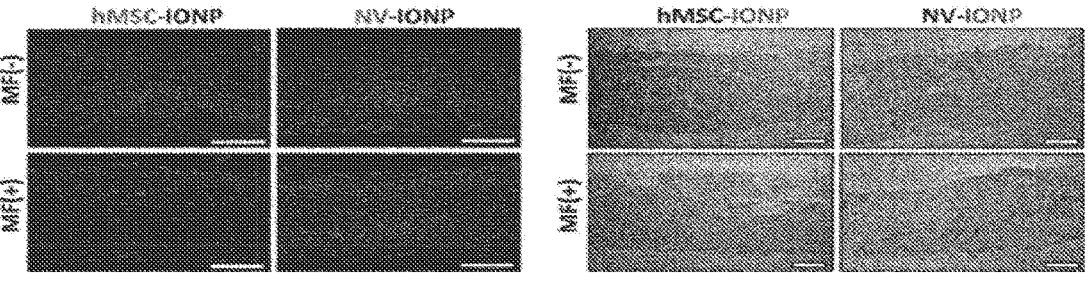

【FIG 21】
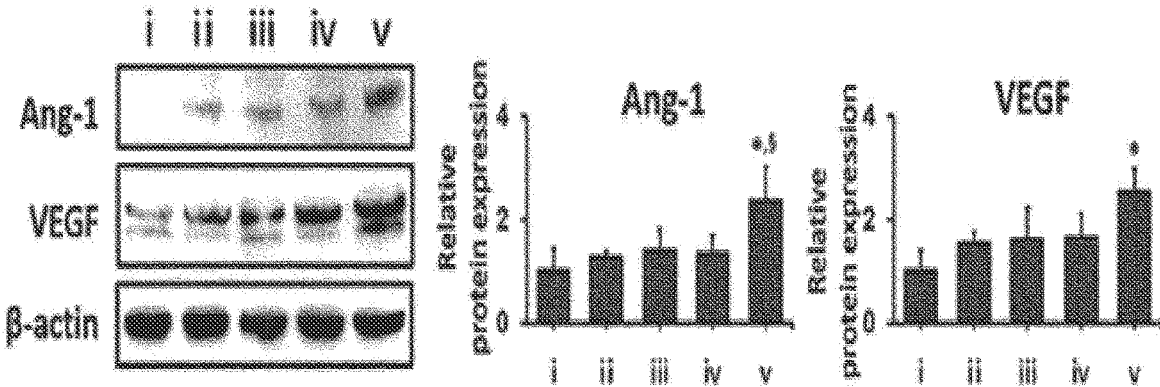
【FIG 22】
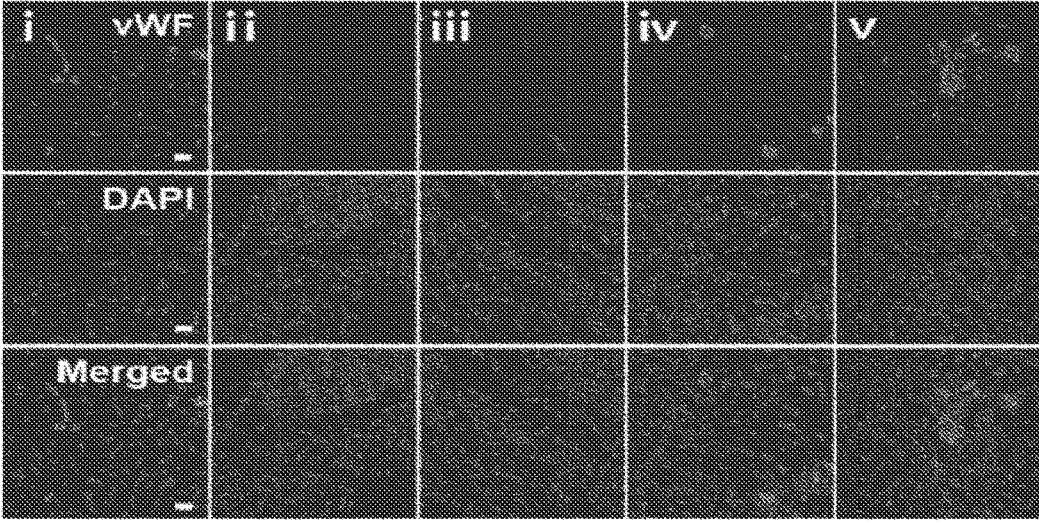

【FIG 23】
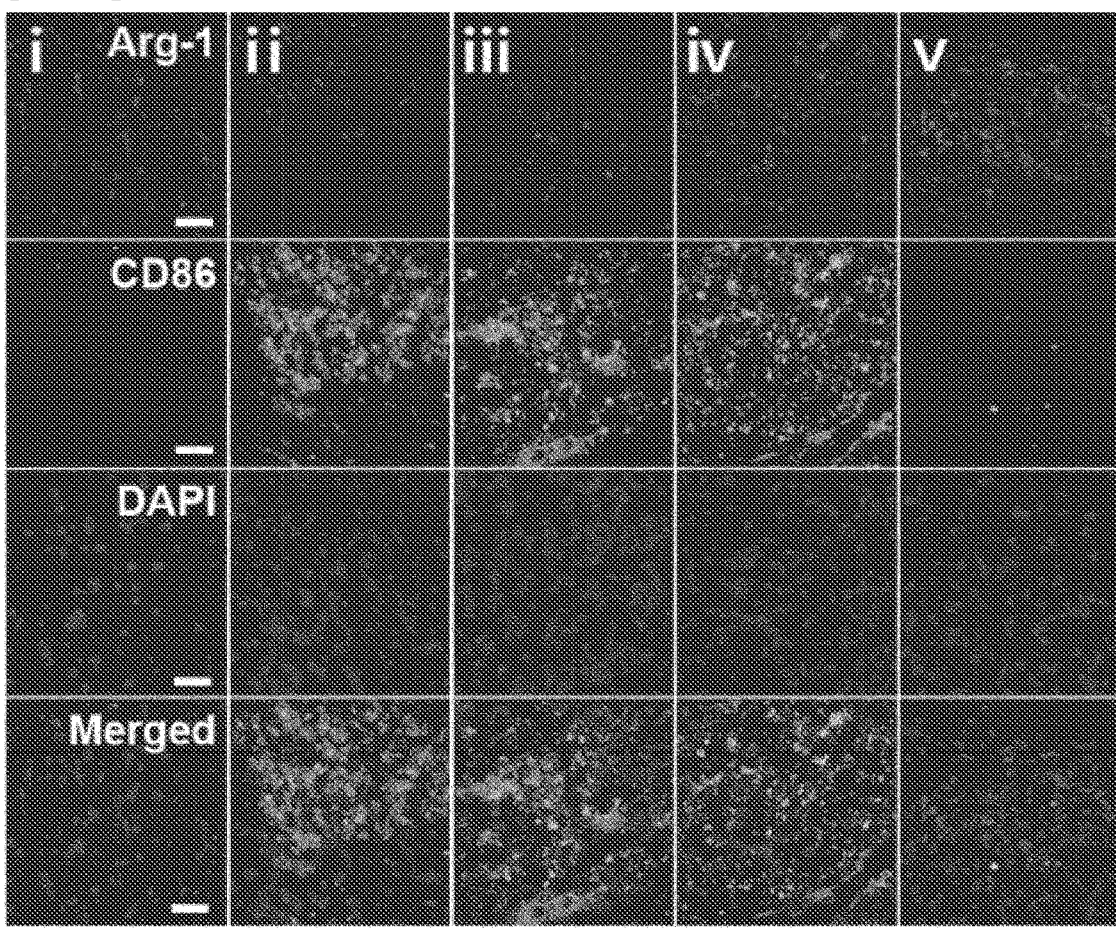
【FIG 24】
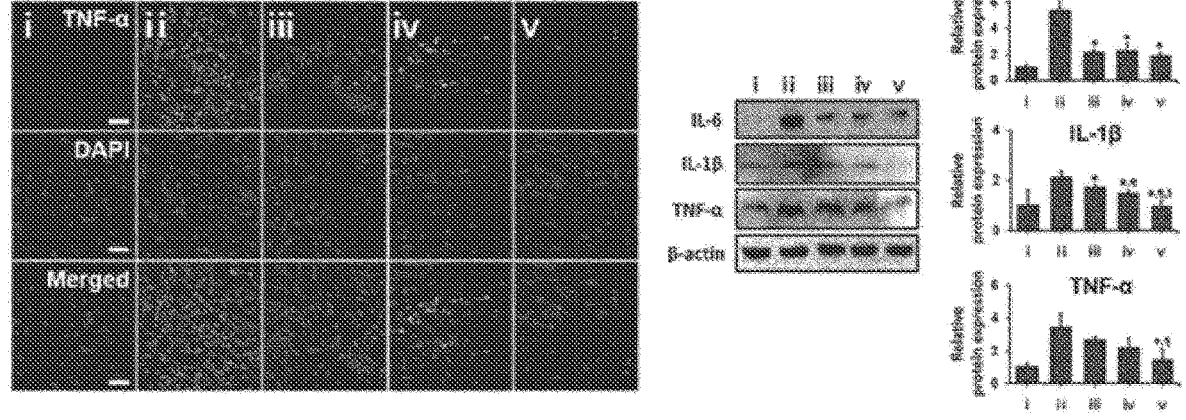

【FIG 25】
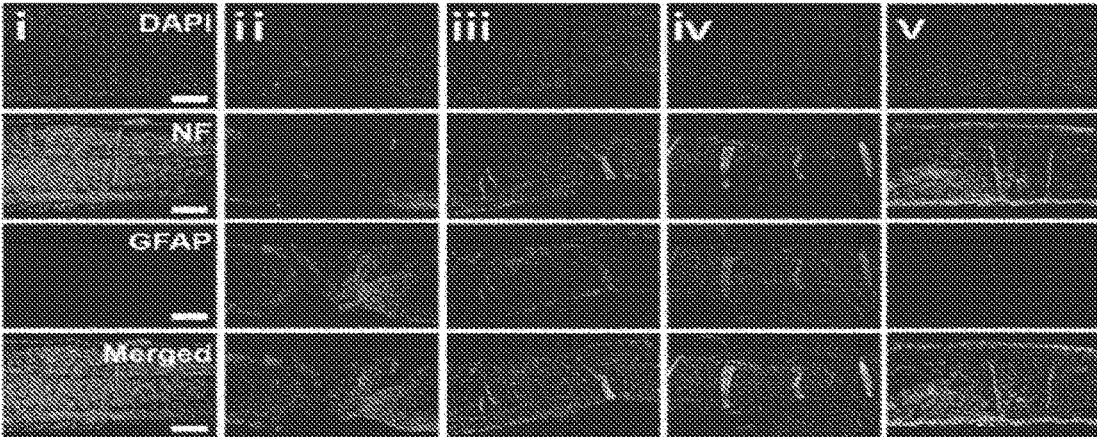
【FIG 26】
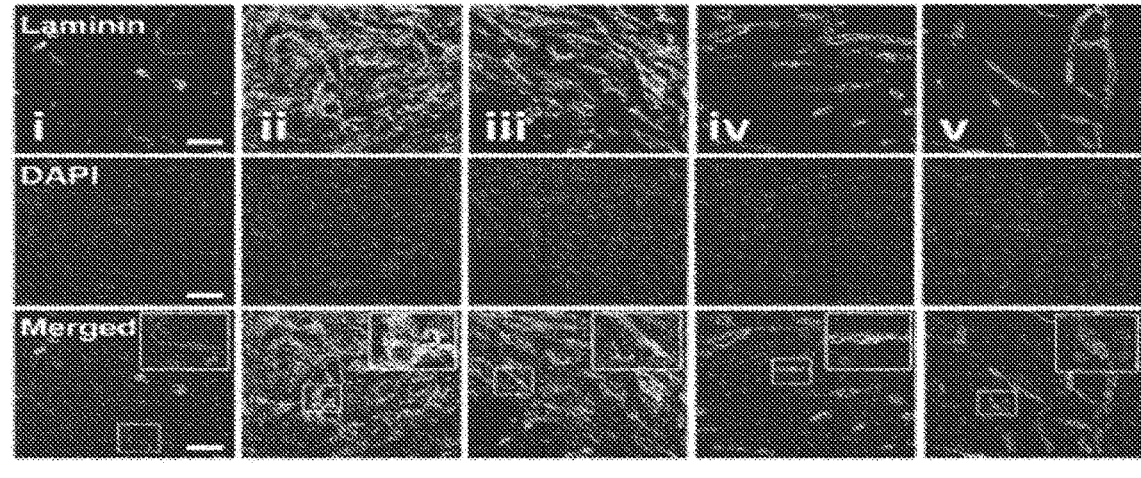
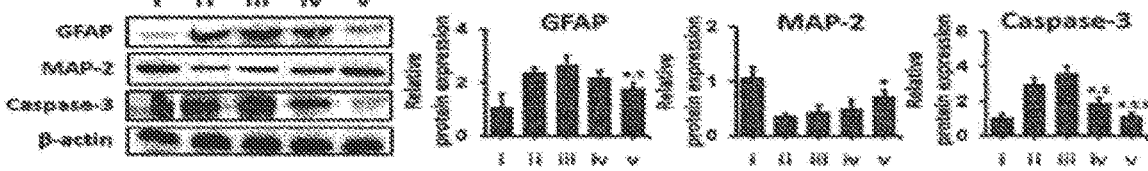
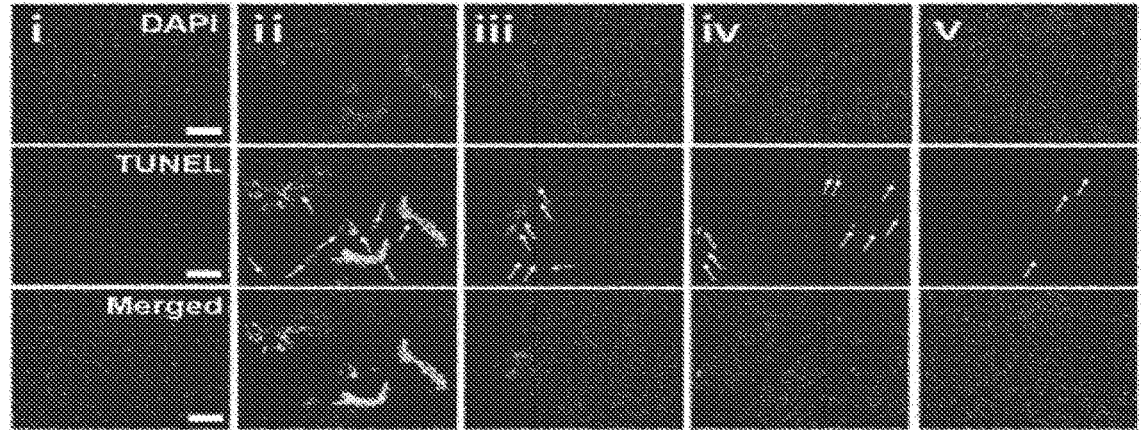

【FIG 27】
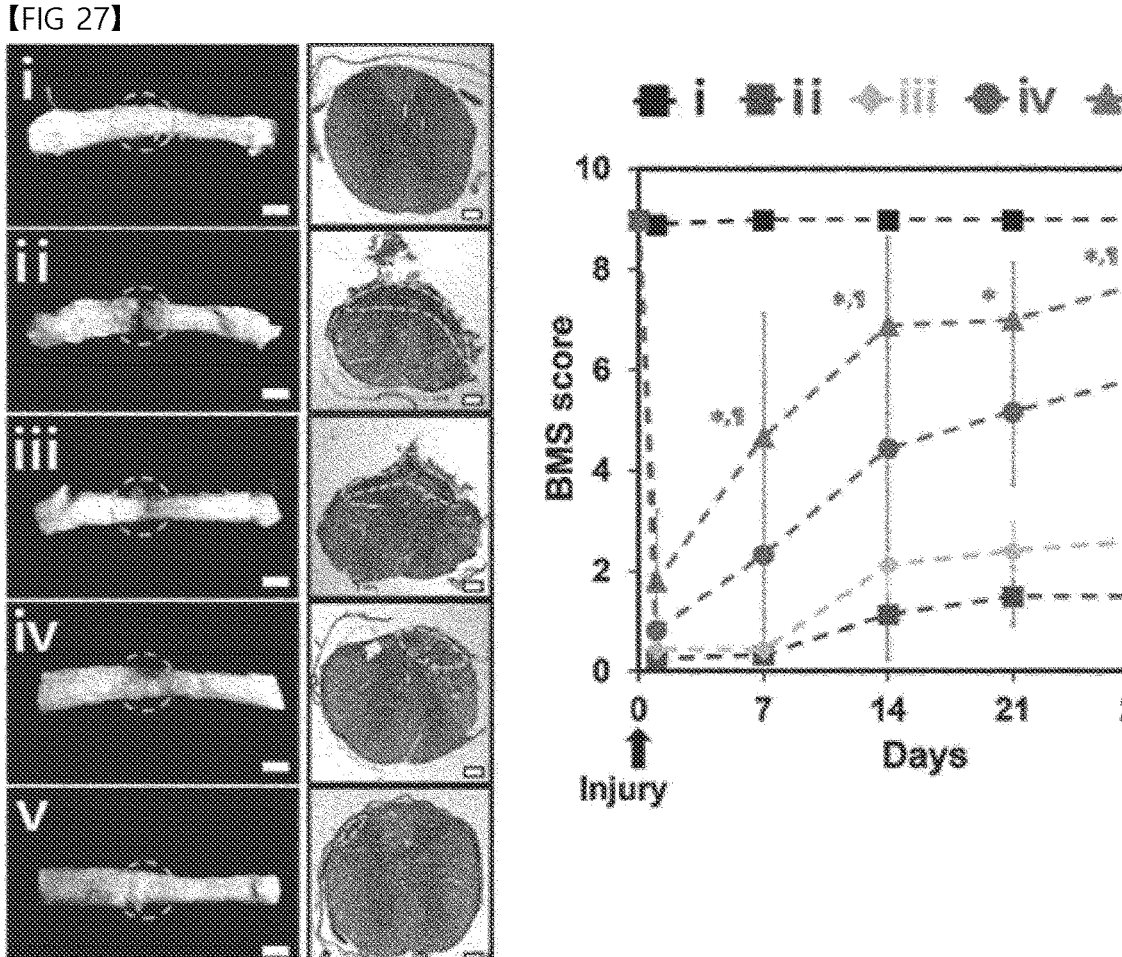

【FIG 28】
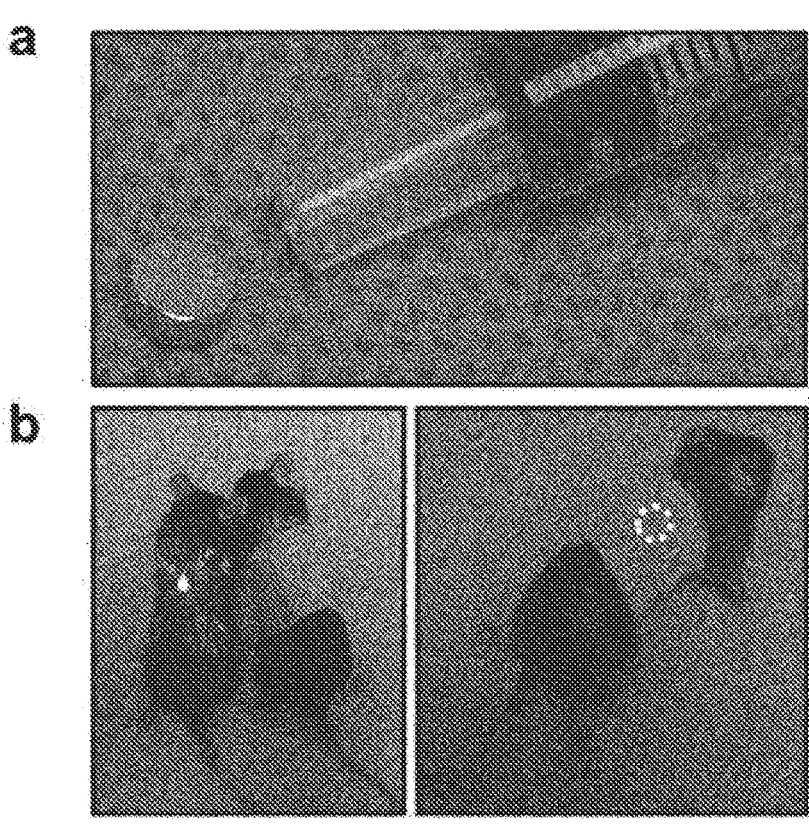

NANOVESICLES FROM ADULT STEM CELLS AND ITS USE FOR TARGETED THERAPY

CROSS-REFERENCE TO RELATED APPLICATION(S)

This application claims priority to KR Patent Application No. 10-2018-0011928 filed on Jan. 31, 2018, and KR Patent Application No. 10-2019-0010380 filed on Jan. 28, 2019, the content of which is hereby incorporated by reference herein.

FIELD OF THE DISCLOSURE

The present disclosure relates to exosomes derived from stem cells and targeted therapy using the same

RELATED ART

Exosomes are vesicles with a size of 50 nm to 200 nm secreted from cells. Since exosomes have genetic or protein information derived from their parent cells, they can deliver the corresponding information to other cells. As such, the exosomes derived from mesenchymal stem cells have a therapeutic efficacy similar to that of mesenchymal stem cells, and thus, a potential of exosomes as a therapeutic agent in the field of cell-free regenerative medicine has been suggested.

Korea Patent Application Publication No. 2018-0003322 (published on Jan. 9, 2018) relates to a composition for promoting angiogenesis, comprising an exosome-mimicking nanovesicle derived from adult stem cells and a method for preparing the same, and a nano-sized vesicle contained in a filtrate of adult stem cells, in which two or more sizes of adult stem cells are sequentially passed from a large filter to a small filter with membrane filters of different sizes.

Korea Patent Application Publication No. 10-2017-0010956 (Published on Feb. 2, 2017) relates to a composition for preventing or treating diabetes comprising a stem cell-derived vesicle as an active ingredient.

However, the composition had no targeting ability for in vivo organs, and systemically administered exosomes were very limited in use because they did not exert sufficient therapeutic effects.

Additionally, due to the nature of exosomes being secreted naturally, a very small amount of exosomes is secreted (1 µg to 4 µg of exosomes are secreted from $10^6$ cells per day based on mesenchymal stem cells), there were limitations in supplying exosomes as a treatment. Additionally, in order to increase target efficiency to an organ in need of treatment, most studies or inventions generally employ a method of direct injection into a disease site, rather than using exosomes as an agent for intravenous injection, but the direction injection has problems in that it is invasive and has poor safety.

Therefore, there is a need for the development of a production technology which is capable of synthesizing nanovesicles as a synthetic exosome in a high yield and which has an increased target efficiency to an organ requiring treatment is required.

SUMMARY OF THE DISCLOSURE

Due to the nature of exosomes being secreted naturally, a very small amount of exosomes is secreted (1 µg to 4 µg of exosomes are secreted from $10^6$ cells per day based on mesenchymal stem cells), there were limitations in supplying exosomes as a treatment. Additionally, most studies or inventions generally employ a method of direct injection into a disease site rather than using exosomes as an agent for intravenous injection, which is invasive and has poor safety. In general, the reason for direct injection is that intravenous injection of exosomes has a low targeting efficiency at the corresponding disease area. Accordingly, the present disclosure synthesizes artificial exosomes (i.e., nanovesicles) in a high yield, and the targeting efficiency also shows an improved effect due to magnet induction by coupling with iron nanoparticles.

Exosomes are vesicles with a size of 50 nm to 200 nm secreted from cells. Since exosomes have genetic or protein information derived from their parent cells, they can deliver the corresponding information to other cells. Accordingly, the exosomes derived from mesenchymal stem cells have a therapeutic efficacy similar to that of mesenchymal stem cells, and are thus widely used in various diseases as an alternative therapeutic agent. The present disclosure was developed with the goal of promoting functional recovery of a spinal cord injury by synthesizing artificial exosomes derived from mesenchymal stem cells (i.e., iron-nanovesicles) to improve targeting efficacy and therapeutic effects after intravenous injection. The present disclosure can replace mesenchymal stem cells as a cell therapeutic agent, and it can be applied to various diseases as a novel biopharmaceutical drug because it can increase the function and efficiency of an exosome-based therapeutic agent.

An aspect of the present disclosure provides an iron nanovesicle derived from adult stem cells containing iron nanoparticles therein.

In an embodiment, the nanovesicle according to the present disclosure is administered to a subject in need of administration of the nanovesicle (e.g., a mammal), particularly considering the characteristics of the nanovesicle according to the present disclosure, is administered intravenously, and after the administration, the nanovesicle is targeted through a step of targeting the administered nanovesicle to an organ or tissue of the subject by applying magnetism to the organ or tissue of the subject.

In an embodiment, the nanovesicle according to the present disclosure is prepared from mesenchymal stem cells.

In an embodiment, 1 µg of the nanovesicle according to the present disclosure contains a high content of about 17 ng of nanoparticles.

In an embodiment, the iron nanoparticles contained in the nanovesicle according to the present disclosure have a diameter in the range of about 10 nm to about 15 nm, and the nanovesicle has a diameter in the range of about 100 nm to about 150 nm, but the diameters of the iron nanoparticles and the nanovesicle are not limited thereto.

In an embodiment, the nanovesicle according to the present disclosure is prepared by a method which includes a step of providing adult stem cells; a step of pretreating the adult stem cells by culturing them in the presence of iron nanoparticles; and a step of sequentially extruding the pretreated adult stem cells using a membrane filter having at least three different pore sizes with a pore size of 10 µm or less in the order of decreasing pore size.

In an embodiment, in the pretreatment step, about $1\times10^6$ cells are adhered and cultured and are treated at a concentration of about 40 µg/mL for about 16 hours.

In an embodiment, the extrusion through a membrane is to sequentially extrude with membrane filters of about 10

µm, about 5 µm, about 1 µm, and about 400 nm pores, and as a result, nanovesicles with a pore size of 150 nm are obtained.

Still another aspect provides a method for preparing a nanovesicle disclosed in the present disclosure, which includes a step of providing adult stem cells; a step of pretreating the adult stem cells by culturing them in the presence of iron nanoparticles; and a step of sequentially extruding the pretreated adult stem cells using a membrane filter having at least four different pore sizes with a pore size of 10 µm or less in the order of decreasing pore size.

In the pretreatment step of the method according to the present disclosure, about $1 \times 10^6$ cells are treated at a concentration of about 40 µg/mL for about 16 hours.

In an embodiment, the extrusion through a membrane is to sequentially extrude with membrane filters of about 10 µm, about 5 µm, about 1 µm, and about 400 nm pores, and as a result, nanovesicles with a pore size of 150 nm are obtained.

In the method according to the present disclosure, the adult stem cells may be prepared from mesenchymal stem cells.

Still another aspect provides a nanovesicle which includes iron nanoparticles prepared according to the method of the present disclosure.

Still another aspect provides a pharmaceutical composition for the treatment of a spinal cord injury containing the nanovesicle which includes iron-nanovesicles disclosed in the present disclosure.

Still another aspect provides a pharmaceutical composition for promoting angiogenesis containing the nanovesicle which includes iron-nanovesicles disclosed in the present disclosure.

Still another aspect provides a pharmaceutical composition for anti-inflammation containing the nanovesicle which includes iron-nanovesicles disclosed in the present disclosure.

Still another aspect provides a pharmaceutical composition for the treatment of stroke or myocardial infarction containing the nanovesicle which includes iron-nanovesicles disclosed in the present disclosure.

In an embodiment, the pharmaceutical composition is each administered intravenously to a subject in need of the administration (e.g., a mammal), and after the administration, the pharmaceutical composition is administered in such a manner that the administered pharmaceutical composition is targeted to a targeted organ or tissue of the subject by applying magnetism to the organ or tissue of the subject.

Still another aspect provides a method for treating a disease, which includes a step of administering the nanovesicle including iron nanoparticles according to the present disclosure or a composition containing the nanovesicle in a therapeutically effective amount to a subject in need of treatment of a disease.

In an embodiment, the treatment of a disease includes, but is not limited to, treatment of a spinal cord injury, diseases requiring promotion of angiogenesis, anti-inflammation, stroke, and myocardial infarction.

BRIEF DESCRIPTION OF THE DRAWINGS

FIG. 1 is a schematic diagram illustrating the synthesis of iron-nanovesicles, targeting of a spinal cord injury site, and treatment results according to the present disclosure.

FIG. 2 is a schematic diagram illustrating the mechanism of treating a spinal cord injury with the iron-nanovesicles according to the present disclosure.

FIG. 3 shows the observation results of iron nanoparticles used in the present disclosure and iron nanoparticles treated to mesenchymal stem cells by a transmission electron microscope (TEM).

FIG. 4 shows the results of cytotoxicity test of the iron nanoparticles used in the present disclosure and the results of the uptake of mesenchymal stem cells (hMSCs).

FIG. 5 shows results illustrating the increase in mRNA expression of growth factors over time after treating cells with iron nanoparticles according to the present disclosure.

FIG. 6 schematically shows the results of the increase in expression of growth factor proteins and its mechanism after treating cells with iron nanoparticles according to the present disclosure and a mechanism thereof.

FIG. 7 shows the results illustrating the purities of proteins and irons in the process of iron-nanovesicles (NV-IONP) synthesis according to the present disclosure.

FIG. 8 shows the observation results of the morphology of iron-nanovesicles (NV-IONP) and nanovesicles (NV) according to the present disclosure under a microscope and the quantification results of iron nanoparticles.

FIG. 9 shows the evaluation results of the size and magnetism of iron-nanovesicle (NV-IONP) and nanovesicles (NVs) according to the present disclosure.

FIG. 10 shows the observation results by a confocal microscope of macrophages treated with nanovesicles (NV) (left) NV and iron-nanovesicles (NV-IONP) (right) according to the present disclosure.

FIG. 11 shows the results of quantifying the amount of growth factor mRNA and protein inside NV and NV-IONP according to the present disclosure.

FIG. 12 shows the evaluation results of angiogenesis after treating vascular endothelial cells (HUVECs) with NV and NV-IONP according to the present disclosure.

FIG. 13 shows the analysis results of the proliferation and migration ability of vascular endothelial cells (HUVECs) treated with NV and NV-IONP according to the present disclosure.

FIG. 14 shows the analysis results of the cellular signaling system of vascular endothelial cells (HUVECs) treated with NV and NV-IONP according to the present disclosure.

FIG. 15 shows the inhibitory effect of NV and NV-IONP according to the present disclosure against PC12 neuronal cell death.

FIG. 16 shows the results of promoting secretion of astrocytes growth factors by NV and NV-IONP according to the present disclosure.

FIG. 17 shows the effect of substituting macrophage phenotypes by NV and NV-IONP (M1 to M2) according to the present disclosure.

FIG. 18 shows the evaluation results of long-term distribution and spinal cord targeting after intravenous injection of mesenchymal stem cells and the nanovesicles according to the present disclosure.

FIG. 19 shows the evaluation (quantification) results of long-term distribution and spinal cord targeting after intravenous injection of mesenchymal stem cells and the nanovesicles according to the present disclosure.

FIG. 20 shows the observation results of the spinal cord tissue (left: observation of nanovesicles, right: observation of iron-nanoparticles) after intravenous injection of mesenchymal stem cells and the nanovesicles according to the present disclosure.

FIG. 21 shows the expression of growth factors in spinal cord tissue after intravenous injection of the iron-nanovesicles according to the present disclosure in a mouse model of spinal cord injury.

FIG. 22 shows the observation results of angiogenesis after injection of the iron-nanovesicles according to the present disclosure in a mouse model of spinal cord injury.

FIG. 23 shows the observation results of the macrophage type (M1 vs. M2) of the tissue of a spinal cord injury.

FIG. 24 shows the analysis results of secretion of the inflammatory cytokines (left: IHC, right: western blot) of the tissue of a spinal cord injury after injection of the iron-nanovesicles according to the present disclosure.

FIG. 25 shows the observation results of the distribution of neurons and astrocytes in the tissue of a spinal cord injury after injection of the iron-nanovesicles according to the present disclosure.

FIG. 26 shows the observation results of the fibrosis progression and cell death of the tissue of a spinal cord injury after injection of the iron-nanovesicles according to the present disclosure.

FIG. 27 shows the evaluation results of the protective effect of the iron-nanovesicles according to the present disclosure on the spinal cord tissue and subsequent recovery of spinal cord function.

FIG. 28 shows images targeting after injection of the iron-nanovesicles according to the present disclosure.

DESCRIPTION OF EXEMPLARY EMBODIMENTS

Conventional exosome technology enables isolation of exosomes naturally secreted from a stable cell line (an animal cell line for mass production) that cannot be used for clinical use or from stem cells without special treatment with a low yield. In contrast, the present disclosure provides effects of maximizing the efficacy of treating mesenchymal stem cells by pretreating cells with iron nanoparticles; reconstituting the cells in a nano-sized form to facilitate intravenous injection; and increasing the efficiency of targeting disease areas through magnet induction. In particular, the present disclosure can replace mesenchymal stem cells as a cell therapeutic agent, and it can be applied to various diseases as a novel biopharmaceutical drug because it can increase the function and efficiency of an exosome-based therapeutic agent.

In this regard, one aspect of the present disclosure relates to iron-nanovesicles derived from adult stem cells containing iron nanoparticles therein.

The nanovesicle according to the present disclosure is administered to a subject in need of administration of the nanovesicle (e.g., a mammal), particularly considering the characteristics of the nanovesicle according to the present disclosure, is administered intravenously, and after the administration, the nanovesicle is targeted through a step of targeting the administered nanovesicle to an organ or tissue of the subject by applying magnetism to the organ or tissue of the subject.

In the present disclosure, a nanovesicle refers to a nano-sized vesicle, which is an artificial exosome or exosome-mimicking vesicle that is similar in characteristics and form to nano-sized exosomes that are naturally produced in cells.

Exosomes, which are nano-sized vesicles naturally produced in cells, contain proteins and genetic information, and are known to be involved in the processes of development, proliferation, differentiation, immune regulation, angiogenesis, progression of various diseases, etc. by delivering various signals including genetic information out of the cell to other cells. Exosomes can be isolated from a variety of cells using techniques known in the art, but the amount that can be isolated is very limited and there was a limitation in their efficacy.

The nanovesicles according to the present disclosure are derived from adult stem cells, particularly mesenchymal stem cells. Adult stem cells are stem cells isolated from bone marrow, blood, dermis, periosteum, etc. and they refer to pluripotent or multipotent cells capable of differentiating into various cells such as adipocytes, chondrocytes, and bone cells.

In an embodiment, the nanovesicles are derived from mesenchymal stem cells. Mesenchymal stem cells are present in bone marrow, etc. in very small amounts, but the processes of isolating and culturing mesenchymal stem cells are well known in the art, for example, they are disclosed in U.S. Pat. No. 5,486,359, the patent document of which is incorporated herein by reference. In addition, the mesenchymal stem cells can be obtained by isolating from the hematopoietic stem cells of the bone marrow according to a known method by a characteristic of attachment, followed by proliferation in a state in which the differentiation ability is not lost. The identification of such mesenchymal stem cells can be performed, for example, through flow cytometry. The flow cytometry is performed using a specific surface marker for mesenchymal stem cells. For example, mesenchymal stem cells show a positive response for CD44, CD29 and/or MHC class I. As the medium used in the above process, any medium generally used for culturing stem cells may be used. Preferably, it is a medium containing serum (e.g., fetal calf serum, equine serum, and human serum). The medium that can be used in the present disclosure include, for example, RPMI Series, Eagle's minimum essential medium (Eagle's MEM, Eagle, H. *Science* 130:432 (1959)), α-MEM (Stanner, C. P. et al., *Nat. New Biol.* 230:52 (1971)), Iscove's MEM (Iscove, N. et al., *J. Exp. Med.* 147:923 (1978)), 199 medium (Morgan et al., Proc. Soc. Exp. Bio. Med., 73:1 (1950)), CMRL 1066, RPMI 1640 (Moore et al., *J. Amer. Med. Assoc.* 199:519 (1967)), F12 (Ham, *Proc. Natl. Acad. Sci. USA* 53:288 (1965)), F10 (Ham, R. G. *Exp. Cell Res.* 29:515 (1963)), Dulbecco's modified Eagle medium (DMEM, Dulbecco, R. et al., VirProcy 8:396 (1959)), a mixture of DMEM and F12 (Barnes, D. et al., *Anal. Biochem.* 102:255 (1980)), Way-mo, h's MB752/1 (Waymo, h, C. *J. Natl. Cancer Inst.* 22:1003 (1959)), McCoy's 5A (McCoy, T. A., et al., *Proc. Soc. Exp. Biol. Med.* 100:115 (1959)), and MCDB Series (Ham, R. G. et al., In Vitro 14:11(1978)), but the medium is not limited thereto. The medium may include other components (for example, antibiotics or antifungal agents (e.g., penicillin, streptomycin), glutamine, etc. General descriptions with respect to media and culture are described in R. Ian Freshney, Culture of Animal Cells, Alan R. Liss, Inc., New York (1984), which is incorporated herein by reference.

The nanovesicles according to the present disclosure include iron nanoparticles.

In an embodiment according to the present disclosure, in preparing exosomes from mesenchymal stem cells, the cells were pretreated with iron-nanoparticles.

As used herein, the term "nanoparticle" or "nano . . . " refers to particles and materials having a dimension of less than about 1,000 nm (e.g., about 100 nm, about 50 nm, about 10 nm, and about 5 nm), and nano-scale materials exhibit different properties from their original properties.

In an embodiment, the diameter of the iron nanoparticles included in nanovesicles according to the present disclosure is in a range of about 10 nm to about 15 nm, and particularly 12 nm. The iron nanoparticles of the above size are less lumped when treated with stem cells, and are thus easily flowed into the cells. In addition, the iron nanoparticles have a size that can be entered in a maximal amount into the nanovesicles prepared in an embodiment of the present disclosure, in particular, the nanovesicles having a diameter of about 100 nm to about 200 nm.

In an embodiment, the nanovesicles according to the present disclosure are located inside the vesicles. In an embodiment, about 17 ng of iron nanoparticles are present in 1 μg of the iron-nanovesicles (NV-IONP) according to the present disclosure.

The iron-nanovesicles according to the present disclosure have a diameter of about 100 nm to about 200 nm, and particularly about 150 nm, thus capable of facilitating intravenous injection.

The iron nanovesicles (NV-IONP) according to the present disclosure can be prepared by the method described below.

In still another aspect, the present disclosure provides a method for preparing nanovesicles including iron-nanoparticles.

In an embodiment, the method includes a step of providing adult stem cells such as mesenchymal stem cells; a step of pretreating the adult stem cells with iron nanoparticles; and a step of sequentially extruding the cells with a membrane filter having different pore sizes with a pore size of about 10 μm or less to prepare iron nanovesicles.

In the method according to the present disclosure, adult stem cells can be referred to those which have been described above. In an embodiment, mesenchymal stem cells are used.

In the method according to the present disclosure, in the pretreatment step, adult stem cells are cultured in a culture medium containing appropriate iron. In an embodiment, about $1 \times 10^6$ adult stem cells are treated with iron nanoparticles at a concentration of about 10 μg/mL to 80 μg/mL. The adult stem cells are treated at a concentration of 10 μg/mL, 20 μg/mL, 40 μg/mL, 50 μg/mL, 60 μg/mL, 70 μg/mL, or 80 μg/mL, but it does not exclude the range therebetween. In an embodiment, the adult stem cells are treated with iron nanoparticles at a concentration of 40 μg/mL, at which exosomes are allowed to contain a large amount of iron without being toxic to the cells. In an embodiment according to the present disclosure, the adult stem cells are treated with iron at the above concentration for about 16 hours, but the conditions with iron treatment are not limited thereto, and the conditions with iron treatment can be determined at a level where a large amount of iron can be contained in exosomes while the cell toxicity of iron can be maintained.

In the method according to the present disclosure, in the extrusion step, the adult stem cells are sequentially extruded into four membrane filters having a pore size of 10 μm or less, in particular 10 μm, 5 μm, 1 μm, and 400 nm. In an embodiment, through the sequential extrusion as described above, it is possible to improve the yield of the nanovesicles and to obtain the nanovesicles of about 150 nm in dimension. Finally, after the 400 nm extrusion, the nanovesicles are finally filtered with a 0.22 μm syringe filter (not extruded) and used.

The method of the present disclosure has the following characteristics, in particular, in the existing method and in an embodiment. That is, in the conventional method, since the phospholipid double layer of nanovesicles acts as an obstacle, the membrane is opened and injected by a method of electroporation, so as to artificially inject iron nanoparticles into nanovesicles after extruding the cells. However, this method requires expensive equipment and there is a high possibility that the proteins and mRNAs in exosomes may be leaked out. However, in the method according to the present disclosure, particularly, living cells are first treated with iron nanoparticles, and as a result, growth factors are increased through cell metabolism, and the increased growth factors are later delivered to the extruded nanovesicles. In the conventional method, where iron nanoparticles are added into the vesicles after the preparation of the vesicles, there is a problem in that the growth factors are certainly not increased, but they are rather leaked out through the open membranes, thereby deteriorating the effects of the nanovesicles.

As such, the iron-nanovesicles according to the present disclosure prepared as described above, can exhibit excellent effects of promoting the production of vascular endothelial cells in vitro, promoting the secretion of growth factors secreted from astrocytes, and in addition, inhibiting apoptosis of neurons and inducing a change in macrophage phenotype from an M1 (inflammatory) type to an M2 (anti-inflammatory) type.

In addition, the iron-nanovesicles according to the present disclosure were shown to maximize NV-IONP targeting and improve treatment efficacy through magnet induction after intravenous injection near the injury site in a model with spinal cord injury.

In this regard, the present disclosure provides a pharmaceutical composition containing iron-nanovesicles according to the present disclosure used in the treatment of various diseases to which the above effects can be effectively applied.

The pharmaceutical composition according to the present disclosure is not particularly limited as long as it is a treatment for a disease in which adult stem cells, particularly mesenchymal stem cells, can be used.

In an embodiment, the iron-nanovesicles according to the present disclosure can promote the production of vascular endothelial cells, promote the secretion of growth factors secreted from astrocytes, and in addition, inhibit apoptosis of neurons and induce a change in macrophage phenotype from an M1 (inflammatory) type to an M2 (anti-inflammatory) type, and the iron-nanovesicles can be used to treat various diseases that require such changes.

In an embodiment, a disease is a spinal cord injury.

Another embodiment, it can be used for the promoting angiogenesis, the treatment of a stroke, or myocardial infarction that requires angiogenic effects.

Still another embodiment, the pharmaceutical composition according to the present disclosure is a composition for anti-inflammation.

Still another embodiment, the pharmaceutical composition according to the present disclosure is a composition for promoting angiogenesis.

Still another embodiment, the pharmaceutical composition according to the present disclosure is a composition for inhibiting neuronal cell death or for treating spinal nerve damage through the inhibition.

Still another aspect provides a pharmaceutical composition for the treatment of a spinal cord injury containing the nanovesicle which includes iron-nanovesicles disclosed in the present disclosure.

Still another aspect provides a pharmaceutical composition for promoting angiogenesis containing the nanovesicle which includes iron-nanovesicles disclosed in the present disclosure.

Still another aspect provides a pharmaceutical composition for anti-inflammation containing the nanovesicle which includes iron-nanovesicles disclosed in the present disclosure.

Still another aspect provides a pharmaceutical composition for the treatment of stroke or myocardial infarction containing the nanovesicle which includes iron-nanovesicles disclosed in the present disclosure.

Each pharmaceutical composition according to the present disclosure is administered to a subject in need of administration of each composition according to the present disclosure (e.g., a mammal including humans, monkeys, mice, etc.), and particularly, administered intravenously, and after the administration, it is administered in such a manner that the administered composition is targeted to an organ or tissue by applying an appropriate magnetism to the target organ or tissue of the subject. The appropriate magnetism is a magnetism that allows the administered composition to be induced in a sufficient amount to a target organ, such as spinal cord, and can easily be determined based on the description of Examples of the present disclosure and knowledge of those skilled in the art.

As used herein, the term "treatment", unless stated otherwise, means to reverse, alleviate, inhibit, or prevent the progression of one or more symptoms of a disease or condition to which the term is applied.

The composition according to the present disclosure contains a therapeutically effective amount of iron nanovesicles. A therapeutically effective amount means an amount necessary to alleviate, improve, or beneficially change one or more symptoms of a neurodegenerative disease.

The composition of the present disclosure includes iron the nanovesicles according to the present disclosure mentioned above as an active ingredient, and in addition, it may further contain a compound that maintains/increases the solubility and/or absorbency of one or more kinds of active ingredients exhibiting the same or similar functions, or active ingredients.

In addition, the iron nanovesicles or compositions according to the present disclosure may be used alone or in combination with surgery, drug therapy, and methods using biological response modifiers.

The composition of the present disclosure may be prepared by including at least one pharmaceutically or physiologically acceptable carrier in addition to the above-mentioned active ingredient.

The carrier used in the present disclosure means a pharmaceutically acceptable carrier, excipient, or stabilizer that is non-toxic to cells or mammals exposed to the dosage and concentration used. Examples of such carriers may include saline; Ringer's solution; buffered saline; buffers (e.g., phosphates, citrates, and other organic acids); antioxidants including ascorbic acid; low molecular weight polypeptides (less than about 10 residues); proteins (e.g., serum albumin, gelatin, and immunoglobulin); hydrophilic polymers (e.g., polyvinylpyrrolidone); amino acids (e.g., glycine, glutamine, asparagine, arginine, and lysine); other carbohydrates including monosaccharides, disaccharides, and glucose, or mannose; chelating agents (e.g., EDTA); sugar alcohols (e.g., mannitol and sorbitol); salt-forming counter ions (e.g., sodium); and(or) nonionic surfactants (e.g., Tween, polyethylene glycol (PEG) and Pluronics.

Other conventional additives such as antioxidants, buffers, and bacteriostatic agents may be added as necessary. In addition, diluents, dispersants, surfactants, binders, and lubricants may be additionally added to formulate into injectable formulations (e.g., aqueous solutions, suspensions, emulsions, etc.), pills, capsules, granules, or tablets. Further, the composition of the present disclosure may be preferably formulated according to each disease or ingredient using an appropriate method in the art or using a method disclosed in the Remington's Pharmaceutical Science (recent edition, Mack Publishing Company, Easton PA).

The method of administration of the iron nanovesicles or composition of the present disclosure is not particularly limited, but a known method of administration of an inhibitor may be applied, and according to a desired method, parenteral administration (e.g., intravenous, subcutaneous, intraperitoneal, or topical application), or particularly, intravenous injection is preferred.

The amount of administration varies widely depending on the patient's weight, age, sex, health status, diet, administration time, administration method, excretion rate, disease severity, etc. and parenteral administration, and in particular, intravenous administration may be preferred, but other routes and means are not excluded. In the case of a typical drug, the administration unit includes, for example, a range of about 0.01 mg to about 100 mg, but it does not exclude the ranges higher or lower than the above range. The daily amount of administration may be about in the amount of 1 μg to 10 g, and it may be administered once or several divided doses daily.

Hereinafter, embodiments are provided to help understanding of the present disclosure. However, the following embodiments are only provided to facilitate the understanding of the present disclosure, and the present disclosure is not limited to the following embodiments.

EXAMPLE 1. PREPARATION OF IRON-NANOVESICLES

Human mesenchymal stem cells (hMSCs; Lonza) ($1 \times 10^6$) cultured in a 150 mm dish (IONP, about 12 nm in size, synthesized by the research team led by Prof. Taeghwan Hyeon, Department of Chemical and Biological Engineering, Seoul National University, Korea) were treated with synthesized iron nanoparticles at a concentration of 40 μg/mL for 16 hours and washed with PBS. A total of ten 150 mm dish cells were used. The iron nanoparticles used showed a circular shape of about 12 nm when their size and shape were observed through a transmission electron microscope (see the image on the left in FIG. 3). In addition, when the mesenchymal stem cells treated with the iron nanoparticles were fixed and observed through a transmission electron microscope, a large amount of iron nanoparticles was observed in the endosome in the cell (see the images in the middle and right in FIG. 3).

Then, after dispersing the mesenchymal stem cells containing the iron nanoparticles (hMSC-IONP) in PBS at a concentration of $2 \times 10^6$ cells/mL, the resultants were sequentially extruded with membrane filters having a size of 10 μm, 5 μm, 1 μm, and 400 nm to produce about 150 nm of nanovesicles (NV).

The purities of proteins and iron used in the iron-nanovesicle (NV-IONP) synthesis process were examined. After performing the density-gradient centrifugation of the solution extruded from the hMSC-IONP, the resulting layers were each collected to quantify the proteins and iron ions, respectively. As a result, it was observed that NV-IONP was located in fraction 2, and iron nanoparticles that could not enter the nanovesicle were separated in fraction 4. Therefore, only fraction 2 was separated and centrifuged again, and pellets were generated through magnet induction, and finally, confirming the presence of NV-IONP in fraction 6, only the iron-nanovesicles (NV-IONP) was separated (see FIG. 7).

The iron-nanovesicles (NV-IONP) were aliquoted in an amount of 500 μL each until use and stored at −75° C. The method of preparing iron-nanovesicles according to the present disclosure is schematically illustrated in FIG. 1.

EXAMPLE 2. TOXICITY ASSESSMENT OF IRON NANOPARTICLES USED IN PREPARATION OF NANOVESICLES IN THE PRESENT DISCLOSURE

Toxicity and uptake of hMSC of iron nanoparticles used in Example 1 were measured. Specifically, the cytotoxicity was analyzed according to the manufacturer's method using the CCK-8 assay (Dojindo, Japan), and as a result, the iron-nanoparticles according to the present disclosure showed no specific toxicity up to a concentration of 40 μg/mL in mesenchymal stem cells (see the graph on the left of FIG. 4, mesenchymal stem cells: hMSC, mesenchymal stem cells treated with iron nanoparticles: hMSC-IONP).

Further, the iron-nanoparticles according to the present disclosure were coupled to RITC (red phosphor), treated with mesenchymal stem cells, and analyzed with a fluorescence microscope. The results showed a uniform distribution the iron-nanoparticles in the cells after binding RITC (red phosphor) to iron-nanoparticles according to the present disclosure, the cells were treated with mesenchymal stem cells and analyzed with a fluorescence microscope to show a uniform distribution in the cells (the image on the right of FIG. 4, mesenchymal stem cells: hMSC, mesenchymal stem cells treated with iron nanoparticles: hMSC-IONP).

EXAMPLE 3. EFFICACY ANALYSIS 1 OF IRON-NANOVESICLES (NV-IONPS) PREPARED IN THE PRESENT DISCLOSURE

As a result of observing the forms of NV and NV-IONP extracted from hMSC and hMSC-IONP with a transmission electron microscope, respectively, as in Example 1, distribution of iron nanoparticles was observed in NV-IONP (the image on the left in FIG. 8). In addition, as a result of quantifying iron ions inside each nanovesicle through induction-coupled plasma mass spectrometry (ICP-MS), it was confirmed that about 17 ng of iron nanoparticles were present in 1 μg of NV-IONP (the graph on the right in FIG. 8). The concentration is high. In the conventional method, since the phospholipid double layer of nanovesicles acts as an obstacle, the membrane is opened and injected by a method of electroporation, so as to artificially inject iron nanoparticles into nanovesicles after extruding the cells. However, this method requires expensive equipment and there is a high possibility that the proteins and mRNAs in exosomes may be leaked out. Further, in the method according to the present disclosure, particularly, living cells are first treated with iron nanoparticles, and as a result, growth factors are increased through cell metabolism, and the increased growth factors are later delivered to the extruded nanovesicles. In the conventional method, where iron nanoparticles are added into the vesicles after the preparation of the vesicles, there is a problem in that the growth factors are certainly not increased, but they are rather leaked out through the open membranes, thereby deteriorating the effects of the nanovesicles.

In addition, as a result of confirming the size of NV and NV-IONP by nanoparticle tracking analysis (NTA), it was found that both nanovesicles have an average size of about 150 nm (see the graph on the left of FIG. 9). In addition, as a result of inducing NV-IONP dispersed in a test tube with a magnet using a neodymium magnet, it was confirmed that most of the NV-IONP is attracted to the neodymium magnet after a certain period of time (see the image on the right in FIG. 9).

In addition, as a result of synthesizing NV-IONP using RITC-iron nanoparticles, and staining phospholipid membranes of NV and NV-IONP with DiO (green phosphor), and then observing under a confocal microscope, the fluorescence of iron nanoparticles (red) and NV (green) were found to overlap in NV-IONP (see the image on the left in FIG. 10), and this result indicates that iron nanoparticles are present in a stable state in the nanovesicle in NV-IONP.

Additionally, macrophages (Raw 264.7 cells, obtained from the Korean Cell Line Bank) were treated with NV and NV-IONP and observed under a confocal microscope 16 hours later. As a result, similarly, red and green fluorescence was found to overlap in the NV-IONP experimental group, and this result indicates that iron nanoparticles in NV-IONP do not leak out during the process of uptake into cells (see the image on the right in FIG. 10).

EXAMPLE 4. EFFICACY ANALYSIS 2 OF IRON-NANOVESICLES (NV-IONPS) PREPARED IN THE PRESENT DISCLOSURE

The NV-IONP prepared in the present disclosure was shown to promote the production of vascular endothelial cells, promote the secretion of growth factors secreted from astrocytes, and in addition, inhibit apoptosis of neurons and induce a change in macrophage phenotype from an M1 (inflammatory) type to an M2 (anti-inflammatory) type.

EXAMPLE 4-1. CONTAINING HIGH CONCENTRATIONS OF GROWTH FACTORS

As in Example 1, human mesenchymal stem cells (hMSCs) were treated with iron nanoparticles at a concentration of 40 μg/mL for 16 hours, and then washed with PBS to remove iron nanoparticles. After culturing the cells for 24 hours and 48 hours, the mRNA expression level of the growth factors expressed in the cells was analyzed using a quantitative reverse transcriptase chain reaction (qRT-PCR) (instrument: StepOnePlus real-time PCR system (Applied Biosystems)). The results are shown in FIG. 5. As shown in the results, it was found that the expression of each growth factor examined increased with the incubation time after treatment. In addition, as a result of analyzing the mRNAs of the growth factors in NV (derived from hMSC) and NV-IONP (derived from hMSC-IONP) with qRT-PCR, it was found that the mRNAs of the growth factors, which were increased in hMSC-IONP, were introduced into NV-IONP (see FIG. 11).

Then, expression patterns at the protein level were performed by Western blot. After treatment with iron nanoparticles, the cells were washed with PBS, incubated for 48 hours, and then proteins were extracted and subjected to Western blot using the antibodies for each growth factor shown in FIG. 6. The results are shown in FIG. 6. To be consistent with the results in FIG. 5, the protein expression of each growth factor was shown to increase. In addition, as a result of performing Western blot to evaluate the amount of growth factor proteins in NV and NV-IONP, it was found that more growth factor proteins were distributed in NV-IONP (see FIG. 11).

In addition, as a result of analyzing the mechanism of the increase in expression of growth factors, it was found that the iron nanoparticles were partially ionized at low pH of endosomes in mesenchymal stem cells, and the ionized iron ions stimulated the JNK/c-Jun cell signaling system to stimulate growth factors so that their secretion could be promoted (see FIG. 6).

EXAMPLE 4-2. EFFECT OF PROMOTING ANGIOGENESIS

Whether a large amount of growth factors in NV-IONP promotes angiogenesis of Human umbilical vein endothelial cells (HUVEC; Lonza) was evaluated. NV and NV-IONP were each treated at 40 µg/mL, and 0.68 µg/mL iron nanoparticles equal to the concentration of the iron nanoparticles in NV-IONP 40 µg/mL were used as another control so as to exclude the effect of iron nanoparticles in NV-IONP. Control is a cell not treated with anything. As a result of incubation for 8 hours in a Matrigel-coated dish in an environment where each additive was present, enhanced angiogenesis was observed in HUVEC cells treated with NV-IONP. As a result of quantitative evaluation, it was found that the number of tubular formation increased in the NV-IONP treatment compared to the NV treatment (see FIG. 12). This result indicates that the NV-IONP according to the present disclosure promotes angiogenesis.

Then, the proliferation rate of HUVEC cells treated with iron nanoparticles (0.68 µg/mL), NV (40 µg/mL), and NV-IONP (40 µg/mL) (analyzed at 24, 48, and 72 hours after the treatment with NV and NV-IONP using the CCK-8 assay mentioned above) and mobility were analyzed by the following wound recovery ability test. The proliferation rate of HUVEC cells treated with NV-IONP was shown to be the fastest, and the cell amount after 72 hours was the highest. In addition, as a result of the wound recovery ability test (in which, after the treatment with NV and NV-IONP, the cells at the bottom were wound in a straight line with a pipette tip and incubated on a serum-free cell culture medium so as to inhibit their proliferation, and how much the scratched straight wound fills up again was observed at regular intervals, and whether cells with a better migration ability can move toward the wound is analyzed), the migration ability of the HUVEC cells treated with NV-IONP was shown to be most active (see FIG. 13). HUVEC is a vascular endothelial cell and is the most frequently used cell when evaluating vascular regeneration angiogenesis as an experiment for cells rather than an experiment for an animal. The above-described excellent effects of the present disclosure of 1) tubularity, 2) proliferation rate, and 3) migration ability (wound recovery test) effects, which are the vascular regeneration effects that can be confirmed in the cell in vitro, actually show high vascular regeneration effects when used in vivo in the spinal cord with damaged blood vessels.

Then, in HUVEC cells treated with iron nanoparticle (0.68 µg/mL), NV (40 µg/mL), and NV-IONP (40 µg/mL), the AKT/ERK signaling system known to be closely involved in angiogenesis, proliferation, and migration ability were analyzed by western blot. As a result, as shown in FIG. 14, it was found that phosphorylation was the highest in the HUVEC treated with NV-IONP. Therefore, it is determined that the NV-IONP according to the present disclosure exhibits the angiogenic effect of HUVEC by activating the AKT/ERK signaling system.

EXAMPLE 4-3. EFFECT OF INHIBITING NEURONAL CELL DEATH

Due to the hypoxic environment caused by vascular damage and inflammation caused by the influx of external macrophages at the site of spinal cord injury, the neurotransmitter system is destroyed by the entry of neurons into the apoptosis stage. Therefore, whether NV and NV-IONP can inhibit neuronal cell death as they transmit growth factors was analyzed.

IONP, NV, and NV-IONP (throughput: iron nanoparticles (0.68 µg/mL), NV (40 µg/mL), and NV-IONP (40 µg/mL)) were each treated on PC 12 cells (Paragon Biotech) for 16 hours, and removed after treatment, and then LPS (inducing inflammation) was treated on the cells (1 µg/mL, 24 hours as well), and cultured for 24 hours under hypoxic conditions (2% $O_2$). The results are described in FIG. 15. In FIG. 15, fluorescein diacetate (FDA) in green represents living cells and ethidium bromide (EB) in red represent dead cells. As shown in FIG. 15, about 50% to about 60% of cell death was observed in untreated cells, whereas the effect of inhibiting cell death was observed in cells treated with NV-IONP. Then, mRNA was extracted from the cells, and mRNAs of apoptosis-inducing factors, Bcl2 Associated X (Bax), and an inhibitory factor (Bcl-2) were analyzed by quantitative reverse transcription PCR (qRT-PCR). As shown in the lower panel of FIG. 15, NV-IONP lowered the inducing factor while increasing the expression of the inhibitory factor.

Then, to examine whether the amount of growth factors secreted from astrocytes is increased by activating astrocytes as NV and NV-IONP deliver growth factors, are used to the gene and the protein actually secreted were analyzed by quantification using qRT-PCR and ELISA.

EXAMPLE 4-4. PROMOTING SECRETION OF ASTROCYTE GROWTH FACTORS

IONP, NV, and NV-IONP were each treated to rat cortex astrocytes (Lonza, primary cells) at concentrations of iron nanoparticles (0.68 µg/mL), NV (40 µg/mL), and NV-IONP (40 µg/mL) for 16 hours and then removed. Then, after 48 hours, the cells were lysed or the cell culture was separated, and qRT-PCR and ELISA (the kit used: Duo Set of R&D Systems) were performed using the manufacturer's method for each of the factors shown in FIG. 16. The results are described in FIG. 15. As a result, it was observed that the astrocytes treated with NV-IONP had the highest amount of growth factor secretion. In addition, the amount of secretion of BDNF (a neuroprotective factor), which is part of the growth factor, was also shown to increase. Astrocytes play a role in physically supporting and biochemically assisting vascular endothelial cells or nerve cells in nerve tissue. When physical injury or infarction occurs in nerve tissue, astrocytes secrete growth factors or neuroprotective factors to restore damaged blood vessels or nerve tissue. Therefore, the secretion of growth factors and neuroprotective factors is promoted by NV-IONP according to the present disclosure, indicating that NV-IONP can effectively promote blood vessel regeneration and protect nerve tissue in a spinal cord injury model.

EXAMPLE 4-5. EFFICACY OF SUBSTITUTION OF PHENOTYPE OF MACROPHAGES

Raw 264.7 cells (a mouse macrophage cell line, the Korea Cell Line Bank) were treated with LPS (200 ng/mL), activated with M1, and then treated with IONP, NV, and NV-IONP (treatment concentration: iron nanoparticle (0.68 µg/mL), NV (40 µg/mL), and NV-IONP (40 µg/mL)) at the above-identified concentration for 16 hours, respectively, and then removed. And after 48 hours, the cells were lysed or the cell culture solution was separated, and qRT-PCR and ELISA (R&D Systems' Duo Set) were performed using the manufacturer's method for each single factor shown in FIG. 17. The results are described in FIG. 17. As a result, it was observed that the M1 markers (TNF-α and IL-6) were decreased in the macrophages treated with NV-IONP, whereas the M2 markers (Arg-1, CD206, IL-10, and VEGF), etc. were increased.

When a spinal cord injury occurs, it is certainly accompanied by severe inflammation. The above experiment was performed in vitro to induce a macrophage cell line, Raw264.7, into inflammatory M1 with LPS, and then confirm whether Raw264.7 was induced into the anti-inflammatory M2 type through NV and NV-IONP treatment. Macrophages are mainly present in the injured spinal cord region as an inflammatory M1 type, and the above experimental results show that nanovesicles are effective in inhibiting inflammation by inducing the cells of the injured spinal cord into an anti-inflammatory M2 type.

EXAMPLE 5. EFFECTS OF ENHANCING TARGETING AND TREATING EFFICACIES IN MODEL WITH SPINAL CORD INJURY

It was confirmed that when the NV-IONP prepared in the present disclosure was intravenously injected into a model of spinal cord injury disease, the NV-IONP targeting was maximized through magnet induction near the injured site and treatment efficacy was improved

EXAMPLE 5-1. PREPARATION OF ANIMAL MODEL FOR SPINAL CORD COMPRESSION 7-10 Week old, 25-30 g C57BLC mice (Orient Bio) were bred within the scope of the Animal Ethics Committee of the College of Medicine, Cha University. Anesthesia was performed by injecting C57BLC mice with zoletil (50 mg/kg, Virbac Laboratories, France) and Rompun® (10 mg/kg, Bayer, Korea) in a 1:1 ratio (1 μL/g). If euthanasia is required, animals were euthanized according to the guidelines (GUIDE FOR THE CARE AND USE OF LABORATORY ANIMALS, the 8th Edition).

The device for causing a spinal cord injury is the application of compression by a weight, and since the device is comprised of the weight of 20 g and the supporting rod, a laminectomy was performed on the thoracic vertebra 10 to remove the lamina, and a spinal cord injury was induced by pressing the spinal cord with a weight having a diameter of 1 mm for 1 minute. Then, the body weight was measured and the hair was removed in a circular shape with a radius of 4 cm around the thoracic region of the mouse. The epilation site was sterilized with 70% alcohol. The surgical site was sterilized with povidone and 70% alcohol. After confirming the location of thoracic vertebra 10 (T10), it was covered with a sterile surgical cloth in which only the surgical site is exposed, and then the outer skin was incised about 2 cm using a surgical knife. The muscle layer to be exposed after the incision was also incised around the T10 area using the surgical knife. When the 10th thoracic spinous process was exposed, the spinous process was removed and the posterior spinal cord in lamina was exposed without damaging the dura meter. Then, the spinal cord was pressed for 1 minute using a weight (20 g).

EXAMPLE 5-2. MAXIMIZATION OF TARGETING USING NV-IONP AND CONFIRMATION 1 OF TREATMENT EFFICACY

After intravenously injecting the NV-IONP prepared in the present disclosure into a model of spinal cord injury disease, it was confirmed that maximizing NV-IONP targeting can be maximized and treatment efficacy can be enhanced through magnet induction near the injury site.

Specifically, hMSC-IONP (mesenchymal stem cells treated with iron nanoparticles, cells obtained 48 hours after treatment with 40 μg/mL of iron nanoparticles, cells were injected $5 \times 10^5$) and NV-IONP (hMSC-IONP-derived nanovesicles (iron-nanovesicles isolated from cells obtained 48 hours after the above treatment, injection of 40 μg) were each stained with a fluorescent dye (VivoTrack 680 (Perkin Elmer)), and then intravenously injected in the amount described above, and organ distribution and spinal targeting were observed as follows with or without magnet induction.

At 24 hours after injection, the spinal cord was separated from the main organs disclosed in FIGS. 18 and 19 to perform fluorescence imaging (eXplore Optix System (Advanced Research Technologies Inc.)). As described in FIG. 18, it was observed that hMSC-IONP could hardly pass through the lung capillaries due to its large size and was accumulated in the lung, whereas NV-IONP showed a relatively high level of liver accumulation due to the nature of the nanoparticles. However, the NV-IONP was not observed to be trapped in the lung due to its small size. When a therapeutic substance is intravenously administered, the therapeutic substance reaches the heart first and then reaches the lung thereafter. When the size of the therapeutic substance is large and accumulates in the capillaries of the lungs, there is a problem in that the breathing becomes weak and the substance is unable to circulate and thus cannot be delivered to the targeted spinal cord region. However, since the iron-nanovesicles of the present disclosure are nano-sized, they can pass through the lung capillaries and can be induced with a magnet to the spinal cord through the blood circulation.

For spinal cord targeting, a neodymium magnet (diameter: 5 mm; and thickness: 2 mm) was used as described in FIG. 28. The magnet was placed on the skin above the injured spinal cord and fixed with a tegaderm film and a self-adhesive bandage. The magnet was fixed for 24 hours and removed after 24 hours. When there were several animals, the magnet could affect other animals, and thus, one animal was raised per cage. As a result of observation of spinal cord targeting efficacy, it was found that hMSC-IONP could not be targeted to the spinal cord in both groups, with or without a magnet. In contrast, NV-IONP showed a significantly higher spinal cord targeting in the presence of magnet induction (see FIGS. 18 and 19). FIG. 19 shows a result of quantitative analysis of the results of FIG. 18 (ROI analysis), and hMSC-IONP was mostly accumulated in the lungs and the liver, whereas NV-IONP was accumulated in the liver, but the spinal cord targeting was increased about two times when magnetic induction was performed. In addition, when the fluorescence amount of the spinal cord was divided by the total long-term fluorescence amount and the amounts of hMSC-IONP and NV-IONP were compared, it was observed that NV-IONP had a targeting efficiency of about 4 times higher even without magnetic induction compared to the hMSC-IONP group, and in the presence of magnet induction, it was observed that the targeting efficiency was increased by about 8 times.

Based on the results of FIGS. 18 and 19, spinal cord tissue was separated from mice to prepare tissue sections to observe fluorescence, as shown in FIG. 20, as in other results, fluorescence was strongly observed in the spinal cord of the mice injected with NV-IONP. Prussian blue staining is a method of staining iron ions in tissues in blue. In the present disclosure, Prussian blue staining was used as a method of detecting IONP contained in hMSC-IONP or NV-IONP, and as a result, a large amount of blue pigments were detected in the spinal cord of mice injected with NV-IONP as in the above results.

EXAMPLE 5-3. ANALYSIS OF GROWTH FACTORS AND ANGIOGENESIS DURING NV-IONP INJECTION ACCORDING TO THE PRESENT DISCLOSURE IN MODEL WITH SPINAL CORD INJURY

After injecting NV and NV-IONP with or without magnet induction in the mice treated as described above, spinal cord tissue was separated on the $14^{th}$ day and the expression of growth factors was observed by western blot. The results are shown in FIG. 21, and as a result, the highest growth factor expression was observed in the NV-IONP (magnet: O) group. Each number in FIG. 21 is as follows: (i) normal mice without treatment (ii) spinal cord injury+PBS (iii) spinal cord injury+NV (iv) spinal cord injury+NV-IONP (magnet: X, not applied) (v) spinal cord injury+NV-IONP (magnet: O; applied).

Then, after the injection of NV and NV-IONP with or without magnet induction, spinal cord tissue was separated on the $28^{th}$ day, and the expression of von Willebrand factor (vWF, a vascular endothelial cell marker) was observed through immunohistochemistry (IHC). The results are shown in FIG. 22. As shown in the results, the highest level of angiogenesis was observed in the NV-IONP (magnet: O) group.

In addition, after the injection of NV and NV-IONP with or without magnet induction, spinal cord tissue was separated on the $28^{th}$ day, and the expression of CD86 (M1 marker) and Arg-1 (M2 marker) was observed through immunohistochemistry (IHC). The results are shown in FIG. 23. As a result, it was confirmed that the NV-IONP (magnet: O) group had the lowest CD86 expression as well as the highest Arg-1 expression.

In addition, by confirming that macrophages are induced from an M1 type to an M2 type by NV and NV-IONP, whether the actual inflammatory cytokines secreted from the spinal cord tissue were reduced was confirmed by IHC and western blot. As a result of observing TNF-α, a representative inflammatory cytokine, by IHC, the lowest TNF-α secretion was observed in the NV-IONP (magnet O) group as shown in FIG. 24, and as a result of western blot, the lowest expression of IL-6, IL-1β, and TNF-α was also observed in the corresponding group.

EXAMPLE 5-4. MAXIMIZATION OF TARGETING USING NV-IONP AND CONFIRMATION 2 OF TREATMENT EFFICACY

(1) Effect of Reducing Astrogliosis

In general, when spinal cord injury occurs, astrogliosis (an abnormal increase in the number of astrocytes due to destruction of adjacent neurons) appears, which destroys the neurotransmitter system by interfering with transmission between neurons. After the injection of NV and NV-IONP, the spinal cord was separated from the spinal cord on the $28^{th}$ day and immunohistochemistry (IHC) was performed for the analysis of neurons in the spinal cord tissue and astrocyte distribution. The analysis was performed by the method of neurofilament (nerve, green) and GFAP (astrogliosis, red). The results are shown in FIG. 25. As shown in the results, the mouse spinal cord injected with NV-IONP (magnet: O) had the lowest astrogliosis (GFAP) but the highest connectivity between neurons (NF). These results indicate that HGF or FGF2 in NV-IONP according to the present disclosure were influential, and simultaneously, astrogliosis was also reduced by the inhibited inflammatory response.

(2) Effects on Fibrosis and Cell Death

A representative symptom accompanied after spinal cord injury is tissue fibrosis, which also interferes with the transmission system between neurons. In addition, neuronal cell death also occurs due to inflammation, astrogliosis, destruction of blood vessels, etc.

In order to confirm the fibrosis by NV and NV-IONP in vivo, the fibrosis marker (laminin) was confirmed in spinal cord tissue after intravenous injection by IHC. The results are shown in FIG. 26. As shown in the results, the lowest fibrosis was observed in the NV-IONP (magnet: O) group. In addition, as a result of analysis using the TUNEL assay according to the manufacturer's method (DeadEnd Fluorometric TUNEL System, Promega) to confirm the cell death of neurons, the smallest number of apoptotic cells were also observed in the NV-IONP (magnet: O) group.

(3) Effect of Protecting Spinal Cord Tissue and Evaluation of Recovery Of Spinal Cord Function The spinal cord tissue isolated on the final $28^{th}$ day after the injection was observed through the effects of the iron-nanovesicles suggested above with respect to promoting angiogenesis, promoting growth factor secretion, anti-inflammation, apoptosis, etc. The results are shown in FIG. 27. As a result of staining transverse tissue sections with Masson's trichrome (fibrosis: green dotted line), preservation of gray matter and white matter was observed to be the best in the experimental group, and fibrosis also proceeded with the smallest area. As a result of quantitative evaluation of spinal cord injury and spinal cord function up to the $28^{th}$ day after the injection of nanovesicles through the behavioral test, the highest recovery of spinal cord function was found in the NV-IONP (magnet: O) group. As shown, it was observed that the thickness and morphology of the spinal cord injury site (green dotted line) in the NV-IONP (magnet: O) group was preserved at a level close to that of normal mice.

The present disclosure was performed with the support of the following research projects:

| Item | Project 1 | Project 2 |
| --- | --- | --- |
| [Project Reference No.] | HR16C0002 | HI18C0183 |
| [Name of Department] | Ministry of Health and Welfare (Korea) | Ministry of Health and Welfare (Korea) |
| [Research Management Institution] | Korea Health Industry Development Institute | Korea Health Industry Development Institute |
| [Name of Research | Fostering of Research- | Researcher-Led Overcoming |

-continued

| Item | Project 1 | Project 2 |
|---|---|---|
| Business] | Driven Hospitals | of Diseases |
| [Name of Research Project] | Construction of Open-Style R&BD Business Platform for Development of Advanced Fusion Type Cell Therapeutic Agent and Its Expansion | Treatment of Acute Spinal Cord Injury using Nanovesicles with Improved Target and Therapeutic Efficacy derived from Cord Blood Stem Cells |
| [Supervising Institution] | Cha University, Bundang Medical Center (Korea) | Seoul National University (Korea) |
| [Research Period] | Apr. 25, 2016 to Dec. 31, 2024 | Apr. 1, 2018 to Dec. 31, 2019 |
| [Rate of Contribution] | 50 | 50 |

ADVANTAGEOUS EFFECTS

The iron-nanovesicle according to the present disclosure has advantages in that it contains iron nanoparticles inside the nanovesicle, and thus, the iron nanoparticles can be stably maintained; that there is a therapeutic effect and less side effects when administered because there is no damage to the cell membrane components constituting the nanovesicle in the preparation process; and that targeting is possible. Compared to the conventional iron nanoparticles attached to the outside of exosomes, there is less damage to the components of the cell membrane. Additionally, exosomes naturally secreted as they are from a stable cell line (an animal cell line for mass production) or from stem cells without special treatment were isolated with a low yield. In contrast, the present disclosure provides effects of maximizing the efficacy of treating mesenchymal stem cells by pretreating cells with iron nanoparticles; reconstituting the cells in a nano-sized form to facilitate intravenous injection; and increasing the efficiency of targeting disease areas through magnet induction. In particular, the present disclosure can replace mesenchymal stem cells as a cell therapeutic agent, and it can be applied to various diseases as a novel biopharmaceutical drug because it can increase the function and efficiency of an exosome-based therapeutic agent.

Although the illustrative examples of the present disclosure have been described in detail above, the scope of the present disclosure is not limited thereto, and various modifications and improved forms thereof by those skilled in the art using the basic concept of the present disclosure defined in the following claims also fall within the scope of the present disclosure.

All technical terms used in the present disclosure, unless defined otherwise, are used in the sense as commonly understood by those skilled in the art in the relevant field of the present disclosure. The contents of all publications described by reference herein are incorporated into the present disclosure.

What is claimed is:

1. An artificial iron-nanovesicle, which is an artificial iron-nanovesicle prepared from an adult stem cell comprising iron nanoparticles therein, wherein the nanovesicle is administered intravenously to a subject, and after the administration, the nanovesicle is targeted through a step of targeting the administered nanovesicle to an organ or tissue of the subject by applying magnetism to the organ or tissue of the subject, wherein iron nanoparticles are contained in the artificial iron-nanovesicle, and have a diameter in the range of 10 nm to 15 nm, and wherein the artificial iron-nanovesicle is prepared by the method comprising:

a step of pretreating the adult stem cells by culturing them in the presence of iron nanoparticles; and a step of sequentially extruding the pretreated adult stem cells with a membrane filter having different pore sizes.

2. The iron-nanovesicle of claim 1, wherein 1 µg of the nanovesicle comprises 17 ng of nanoparticles.

3. The iron-nanovesicle of claim 1, wherein the adult stem cell is a mesenchymal stem cell.

4. The iron-nanovesicle of claim 1, wherein the nanovesicle has a diameter in the range of 100 nm to 150 nm.

5. A method for preparing a nanovesicle comprising iron nanoparticles therein, wherein the method for preparing the nanovesicle according to claim 1 comprises:

a step of providing adult stem cells;

a step of pretreating the adult stem cells by culturing them in the presence of iron nanoparticles; and a step of sequentially extruding the pretreated adult stem cells with a membrane filter having at least four different pore sizes with a pore size of 10 µm or less in the order of decreasing pore size.

6. The method of claim 5, wherein in the pretreatment step, $1 \times 10^6$ cells are treated with iron nanoparticles at a concentration of 40 µg/mL for 16 hours.

7. The method of claim 5, wherein the extrusion is performed such that the pretreated adult stem cells are sequentially extruded with a membrane filter having a pore size of 10 µm, 5 µm, 1 µm, and 400 nm, and nanovesicles having a pore size of 150 nm are obtained as a result.

8. The method of claim 5, wherein the adult stem cells are mesenchymal stem cells.

9. An artificial iron-nanovesicle comprising the iron nanoparticles prepared by a method, comprising:

a step of providing adult stem cells;

a step of pretreating the adult stem cells by culturing them in the presence of iron nanoparticles; and a step of sequentially extruding the pretreated adult stem cells with a membrane filter having at least four different pore sizes with a pore size of 10 µm or less in the order of decreasing pore size, and wherein iron nanoparticles are contained in the artificial iron-nanovesicle, and have a diameter in the range of 10 nm to 15 nm.

10. A pharmaceutical composition for the treatment of a spinal cord injury comprising the artificial iron-nanovesicle of claim 1.

11. A pharmaceutical composition for promoting angiogenesis, comprising the artificial iron-nanovesicle of claim 1.

12. A pharmaceutical composition for anti-inflammation comprising the artificial iron-nanovesicles of claim 1.

13. A pharmaceutical composition for the treatment of stroke or myocardial infarction comprising the artificial iron-nanovesicle of claim 1.

14. The pharmaceutical composition according to claim 10, wherein the pharmaceutical composition is administered intravenously to a subject, and after the administration, the pharmaceutical composition is administered in such a manner that targeted the administered pharmaceutical composition is targeted to a targeted organ or tissue of the subject by applying magnetism to the organ or tissue of the subject.

15. The artificial iron-nanovesicle of claim 9, wherein in the pretreatment step, $1 \times 10^6$ cells are treated with the iron nanoparticles at a concentration of 40 μg/mL for 16 hours.

16. The artificial iron-nanovesicle of claim 9, wherein the extrusion is performed such that the pretreated adult stem cells are sequentially extruded with a membrane filter having a pore size of 10 μm, 5 μm, 1 μm, and 400 nm, and nanovesicles having a pore size of 150 nm are obtained as a result.

17. The artificial iron-nanovesicle of claim 9, wherein the adult stem cells are mesenchymal stem cells.

\* \* \* \* \*